US006867289B1

(12) United States Patent
Gorenstein et al.

(10) Patent No.: US 6,867,289 B1
(45) Date of Patent: Mar. 15, 2005

(54) THIO-MODIFIED APTAMER SYNTHETIC METHODS AND COMPOSITIONS

(75) Inventors: David G. Gorenstein, Houston, TX (US); Bruce A. Luxon, Galveston, TX (US); Norbert Herzog, Friendswood, TX (US); Judy Aronson, Galveston, TX (US)

(73) Assignee: Board of Regents, The University of Texas Systems, Austin, TX (US)

(*) Notice: Subject to any disclaimer, the term of this patent is extended or adjusted under 35 U.S.C. 154(b) by 0 days.

(21) Appl. No.: 09/425,804

(22) Filed: Oct. 25, 1999

Related U.S. Application Data

(60) Provisional application No. 60/105,600, filed on Oct. 26, 1998.

(51) Int. Cl.⁷ .......................... C07H 21/04; C07K 14/00
(52) U.S. Cl. ....................................... 536/23.1; 530/350
(58) Field of Search .............................. 536/23.1, 25.4; 435/6, 91.2; 530/350; 436/501; 514/44

(56) References Cited

U.S. PATENT DOCUMENTS

| | | | |
|---|---|---|---|
| 5,218,088 A | 6/1993 | Gorenstein et al. | 536/25.34 |
| 5,397,698 A | 3/1995 | Goodman et al. | 435/6 |
| 5,576,302 A | 11/1996 | Cook et al. | 514/44 |
| 5,587,361 A | 12/1996 | Cook et al. | 514/44 |
| 5,599,797 A | 2/1997 | Cook et al. | 514/44 |
| 5,602,000 A | 2/1997 | Hyman | 435/91.1 |
| 5,607,923 A | 3/1997 | Cook et al. | 514/44 |
| 5,620,963 A | 4/1997 | Cook et al. | 514/44 |
| 5,635,488 A | 6/1997 | Cook et al. | 514/44 |
| 5,639,873 A | 6/1997 | Barascut et al. | 536/25.3 |
| 5,660,985 A | 8/1997 | Kirschenheuter et al. | |
| 5,661,134 A | 8/1997 | Cook et al. | 514/44 |
| 5,705,337 A | 1/1998 | Gold et al. | 435/6 |
| 5,734,041 A | 3/1998 | Just et al. | 536/25.31 |
| 5,763,595 A | 6/1998 | Gold et al. | 435/22.1 |
| 5,795,721 A | 8/1998 | Rabin et al. | 435/6 |
| 5,804,445 A | 9/1998 | Brasier | 435/375 |
| 5,874,219 A | 2/1999 | Rava et al. | 435/6 |

FOREIGN PATENT DOCUMENTS

| | | | |
|---|---|---|---|
| WO | WO 92 14842 A | | 9/1992 |
| WO | WO 92/14843 | * | 9/1992 |
| WO | WO 93 08296 A | | 4/1993 |
| WO | WO 96 19572 A | | 6/1996 |

OTHER PUBLICATIONS

Selection and Characterization of an RNA Decoy for Transcription Factor NF–xB, *Biochemistry* 1999, 38, pp. 3168–3174.

Novel Combinatorial Selection of Phosphorothioate Oligonucleotide Aptamers, *Biochemistry* 1998, 37, pp. 16489–16493.

Oligonucleotide Analogues as Potential Chemotherapeutic Agents, *Pharmaceutical Research*, vol. 5, No. 9, 1988, pp. 539–549.

Bielinska A et al: "Regulation of Gene Expression with Double–Stranded Phosphorothioate Oligonucleotides" Science, American Association for the Advancement of Science,, US, vol. 250, Nov. 16, 1990, pp. 997–1000, XP002065516 ISSN: 0036–8075.

Kunsch, Charles et al: "Selection of optimal.kappa.B/Rel DNA–binding motifs: interaction of bot subunits of NF–.kappa.B with DNA is required for transcriptional activation" Molecular and Cellular Biology ( 1992 ), 12(10), 4412–2, XP009003474.

Antsypovich, Sergei et al: "Cross–linked DNA duplexes. Exonuclease stability and interactio with the nucleic transcription factor of the .kappa. light–chai enhancer (NF–.kappa. B )" European Journal of Biochemistry (1998), 255(2), 414–421, XP002226148.

Sharma, H.W. et al.: "Transcription factor decoy approach to decipher the role of NF–KB in oncogenesis" Anticancer Research, vol. 16, 1996, pp. 61–70, XP009003192.

Morishita, R.M. et al.: "In vivo transfection of cis element "decoy" against nuclear factor–kB binding site prevents myocardial infarction" Nature Medicine, vol. 3, No. 8, 1997, pp. 894–899, XP009003193.

Khaled, Annette R. et al: "Use of phosphorothioate –modified oligodeoxynucleotides to inhibit NF–kappa. B expression and lymphocyte function" Clinical Immunology and Immunopathology (1998), 86(2), 170–179, XP009003515.

Stec, W.J. et al.: "Deoxyribonucleoside 3'–0–(2–thio–and 2–oxo–"spiro"–4,4–pentamethylene–1,3,2–oxathiaphospholane)s" J. Am. Chem. Soc. , vol. 120, 1998, pp. 7156–7167, XP002239290.

Uhlmann E et al: "Studies on the Mechanism of Stabilization of Partially Phosphorothioated Oligonucleotides Against Nucleolytic Degradation" Antisense & Nucleic Acid Drug Development, Mary Ann Liebert, Inc., New York, US, vol. 7, No. 4, Aug. 1997, pp. 345–350, XP001117604 ISSN: 1087–2906.

Nakamaye, Kay L. et al: "Direct sequencing of polymerase chain reaction amplified DNA fragments through the incorporation of deoxynucleoside.alpha.–thiotriphosphates" Nucleic Acids Research (1988), 16(21), 9947–59, 1988, XP001097564.

* cited by examiner

*Primary Examiner*—Stephanie Zitomer
(74) *Attorney, Agent, or Firm*—Edwin S. Flores; Chalker Flores LLP

(57) ABSTRACT

This invention generally relates the generation of aptamers and to the use of aptamers as diagnostic and therapeutic agents. More particularly, the present invention relates to methods using combinatorial chemistry to prepare aptamers having controlled thiophosphate replacement in the phosphate backbone for improved binding efficiencies to a target and to RNA and/or DNA products having novel nucleotide sequences and enhanced target binding efficacies.

21 Claims, 7 Drawing Sheets

1) 5'GGG GCG GGG GGA$_S$ TA$_S$T GGA$_S$ CAC C3'   (SEQ ID 20)
   3'CCC CTC CCC CCT A$_S$TA$_S$ CCT GTG G5'

2) 5'GGG CTG GTG TGG TA$_S$G A$_S$CT CCC C3'   (SEQ ID 21)
   3'CCC GA$_S$C CA$_S$C A$_S$CC A$_S$TC TGA$_S$ GGG G5'

3) 5'CCC GCC CA$_S$C A$_S$CA$_S$ CA$_S$C CGC CCC C3'   (SEQ ID 22)
   3'GGG CGG CTG TGT GTG GCG GGG G5'

4) 5'GGG CCG GGA$_S$ GA$_S$G A$_S$A$_S$C A$_S$TA$_S$ GCG A$_S$C3'   (SEQ ID 23)
   3'CCC GGC CCT CTC TTG TA$_S$T CGC TG5'

5) 5'CCC NCN NNC A$_S$CA$_S$ CA$_S$C CGC CCC C3'   (SEQ ID 24)
   3'GGG NGN NNG TGT GTG GCG GGG G5'

6) 5'GGT A$_S$TA$_S$ CTC TCC GCC CCT CCC C3'   (SEQ ID 25)
   3'CCA$_S$ TA$_S$T GA$_S$G A$_S$GG CGG GGA$_S$ GGG G5'

7) 5'CCC A$_S$CA$_S$ TGT A$_S$CA$_S$ CGC CGC CCC CGC CC3'   (SEQ ID 26)
   3'GGG TGT A$_S$CA$_S$ TGT GCG GCG GGG GCG GG5'

8) 5'CCC A$_S$CA$_S$ TGN A$_S$CA$_S$ CNC CGC CCC C3'   (SEQ ID 27)
   3'GGG TGT A$_S$CN TGT GNG GCG GGG G5'

FIG. 7A

GGGCG T A$_S$TA$_S$T G* TGTG GCGGG GG   (SEQ ID 28)

FIG. 7B

NATURAL DNA:
Y=O, X=O

THIOPHOSPHATE:
Y=O, X=S

DITHIOPHOSPHATE:
Y=S, X=S

B=THYMINE, ADENINE, CYTOSINE OR GUANINE

THYMIDINE 3'-O-PHOSPHORODITHIOATE

SEQUENCE LISTING

<160> NUMBER OF SEQ ID NOS: 57

<210> SEQ ID NO 1
<211> LENGTH: 67
<212> TYPE: DNA
<213> ORGANISM: Artificial Sequence
<220> FEATURE:
<223> OTHER INFORMATION: Aptamer
<220> FEATURE:
<221> NAME/KEY: misc_feature
<222> LOCATION: (24)..(46)
<223> OTHER INFORMATION: n = a, t, c or g

<400> SEQUENCE: 1
cagtgctcta gaggatccgt gacnnnnnnn nnnnnnnnnn nnnnnncgaa gcttatcgat    60
ccgagcg                                                              67

<210> SEQ ID NO 2
<211> LENGTH: 22
<212> TYPE: DNA
<213> ORGANISM: Artificial Sequence
<220> FEATURE:
<223> OTHER INFORMATION: Aptamer

<400> SEQUENCE: 2
gccgtccaca tacgacacca cc                                              22

<210> SEQ ID NO 3
<211> LENGTH: 22
<212> TYPE: DNA
<213> ORGANISM: Artificial Sequence
<220> FEATURE:
<223> OTHER INFORMATION: Aptamer

<400> SEQUENCE: 3
ggccgaccgc acagcacaac cc                                              22

<210> SEQ ID NO 4
<211> LENGTH: 22
<212> TYPE: DNA
<213> ORGANISM: Artificial Sequence
<220> FEATURE:
<223> OTHER INFORMATION: Aptamer

<400> SEQUENCE: 4
ggcgcggata caacccacac gc                                              22

<210> SEQ ID NO 5
<211> LENGTH: 22
<212> TYPE: DNA
<213> ORGANISM: Artificial Sequence
<220> FEATURE:
<223> OTHER INFORMATION: Aptamer

<400> SEQUENCE: 5
gggcccgctg tacatgcaca cg                                              22

<210> SEQ ID NO 6
<211> LENGTH: 22
<212> TYPE: DNA
<213> ORGANISM: Artificial Sequence
<220> FEATURE:
<223> OTHER INFORMATION: Aptamer

<400> SEQUENCE: 6

```
gggcccgctg tacatgcaca cg                                              22

<210> SEQ ID NO 7
<211> LENGTH: 22
<212> TYPE: DNA
<213> ORGANISM: Artificial Sequence
<220> FEATURE:
<223> OTHER INFORMATION: Aptamer

<400> SEQUENCE: 7
gggcccgctg cacgtgcaca cg                                              22

<210> SEQ ID NO 8
<211> LENGTH: 22
<212> TYPE: DNA
<213> ORGANISM: Artificial Sequence
<220> FEATURE:
<223> OTHER INFORMATION: Aptamer

<400> SEQUENCE: 8
gggcccgctg tacacgcaca cg                                              22

<210> SEQ ID NO 9
<211> LENGTH: 22
<212> TYPE: DNA
<213> ORGANISM: Artificial Sequence
<220> FEATURE:
<223> OTHER INFORMATION: Aptamer

<400> SEQUENCE: 9
cccgttgttg tcccactcca cg                                              22

<210> SEQ ID NO 10
<211> LENGTH: 22
<212> TYPE: DNA
<213> ORGANISM: Artificial Sequence
<220> FEATURE:
<223> OTHER INFORMATION: Aptamer

<400> SEQUENCE: 10
cccgttgttg tcccgctcca cg                                              22

<210> SEQ ID NO 11
<211> LENGTH: 10
<212> TYPE: DNA
<213> ORGANISM: Artificial Sequence
<220> FEATURE:
<223> OTHER INFORMATION: Aptamer

<400> SEQUENCE: 11
gttgcgcaac                                                            10

<210> SEQ ID NO 12
<211> LENGTH: 10
<212> TYPE: DNA
<213> ORGANISM: Artificial Sequence
<220> FEATURE:
<223> OTHER INFORMATION: Aptamer

<400> SEQUENCE: 12
gctgtacatg                                                            10

<210> SEQ ID NO 13
<211> LENGTH: 10
<212> TYPE: DNA
```

-continued

```
<213> ORGANISM: Artificial Sequence
<220> FEATURE:
<223> OTHER INFORMATION: Aptamer

<400> SEQUENCE: 13
gttgtcccac                                                            10

<210> SEQ ID NO 14
<211> LENGTH: 10
<212> TYPE: DNA
<213> ORGANISM: Artificial Sequence
<220> FEATURE:
<223> OTHER INFORMATION: Aptamer

<400> SEQUENCE: 14
gttgttgtcc                                                            10

<210> SEQ ID NO 15
<211> LENGTH: 22
<212> TYPE: DNA
<213> ORGANISM: Artificial Sequence
<220> FEATURE:
<223> OTHER INFORMATION: Aptamer

<400> SEQUENCE: 15
cgtgtgcatg tacagcgggc cc                                              22

<210> SEQ ID NO 16
<211> LENGTH: 42
<212> TYPE: DNA
<213> ORGANISM: Artificial Sequence
<220> FEATURE:
<223> OTHER INFORMATION: Aptamer

<400> SEQUENCE: 16
ccaggagatt ccacccagga gattccaccc aggagattcc ac                        42

<210> SEQ ID NO 17
<211> LENGTH: 14
<212> TYPE: DNA
<213> ORGANISM: Artificial Sequence
<220> FEATURE:
<223> OTHER INFORMATION: Aptamer

<400> SEQUENCE: 17
ccaggagatt ccac                                                       14

<210> SEQ ID NO 18
<211> LENGTH: 10
<212> TYPE: DNA
<213> ORGANISM: Artificial Sequence
<220> FEATURE:
<223> OTHER INFORMATION: Aptamer

<400> SEQUENCE: 18
ggggacttcc                                                            10

<210> SEQ ID NO 19
<211> LENGTH: 62
<212> TYPE: DNA
<213> ORGANISM: Artificial Sequence
<220> FEATURE:
<223> OTHER INFORMATION: Aptamer
<220> FEATURE:
<221> NAME/KEY: misc_feature
<222> LOCATION: (19)..(41)
<223> OTHER INFORMATION: n = a, c, t, or g
```

```
<400> SEQUENCE: 19
atgcttccac gagcctttcn nnnnnnnnnn nnnnnnnnnn nctgcgaggc ggtagtctat    60
tc                                                                    62

<210> SEQ ID NO 20
<211> LENGTH: 22
<212> TYPE: DNA
<213> ORGANISM: Artificial Sequence
<220> FEATURE:
<223> OTHER INFORMATION: Aptamer

<400> SEQUENCE: 20
ggggcggggg gatatggaca cc                                              22

<210> SEQ ID NO 21
<211> LENGTH: 22
<212> TYPE: DNA
<213> ORGANISM: Artificial Sequence
<220> FEATURE:
<223> OTHER INFORMATION: Aptamer

<400> SEQUENCE: 21
gggctggtgt ggtagactcc cc                                              22

<210> SEQ ID NO 22
<211> LENGTH: 22
<212> TYPE: DNA
<213> ORGANISM: Artificial Sequence
<220> FEATURE:
<223> OTHER INFORMATION: Aptamer

<400> SEQUENCE: 22
cccgcccaca cacaccgccc cc                                              22

<210> SEQ ID NO 23
<211> LENGTH: 23
<212> TYPE: DNA
<213> ORGANISM: Artificial Sequence
<220> FEATURE:
<223> OTHER INFORMATION: Aptamer

<400> SEQUENCE: 23
gggccgggag agaacatagc gac                                             23

<210> SEQ ID NO 24
<211> LENGTH: 22
<212> TYPE: DNA
<213> ORGANISM: Artificial Sequence
<220> FEATURE:
<223> OTHER INFORMATION: Aptamer
<220> FEATURE:
<221> NAME/KEY: misc_feature
<222> LOCATION: (4)..(4)
<223> OTHER INFORMATION: n = a, c, t, or g
<220> FEATURE:
<221> NAME/KEY: misc_feature
<222> LOCATION: (6)..(8)
<223> OTHER INFORMATION: n = a, c, t, or g

<400> SEQUENCE: 24
cccncnnnca cacaccgccc cc                                              22

<210> SEQ ID NO 25
<211> LENGTH: 22
<212> TYPE: DNA
```

```
<213> ORGANISM: Artificial Sequence
<220> FEATURE:
<223> OTHER INFORMATION: Aptamer

<400> SEQUENCE: 25
ggtatactct ccgcccctcc cc                                          22

<210> SEQ ID NO 26
<211> LENGTH: 26
<212> TYPE: DNA
<213> ORGANISM: Artificial Sequence
<220> FEATURE:
<223> OTHER INFORMATION: Aptamer

<400> SEQUENCE: 26
cccacatgta cacgccgccc ccgccc                                      26

<210> SEQ ID NO 27
<211> LENGTH: 22
<212> TYPE: DNA
<213> ORGANISM: Artificial Sequence
<220> FEATURE:
<223> OTHER INFORMATION: Aptamer
<220> FEATURE:
<221> NAME/KEY: misc_feature
<222> LOCATION: (9)..(9)
<223> OTHER INFORMATION: n = a, c, t, or g
<220> FEATURE:
<221> NAME/KEY: misc_feature
<222> LOCATION: (14)..(14)
<223> OTHER INFORMATION: n = a, c, t, or g

<400> SEQUENCE: 27
cccacatgna cacnccgccc cc                                          22

<210> SEQ ID NO 28
<211> LENGTH: 22
<212> TYPE: DNA
<213> ORGANISM: Artificial Sequence
<220> FEATURE:
<223> OTHER INFORMATION: Aptamer

<400> SEQUENCE: 28
gggcgtatat gtgtggcggg gg                                          22

<210> SEQ ID NO 29
<211> LENGTH: 14
<212> TYPE: DNA
<213> ORGANISM: Artificial Sequence
<220> FEATURE:
<223> OTHER INFORMATION: Aptamer

<400> SEQUENCE: 29
gtggaatctc ctgg                                                   14

<210> SEQ ID NO 30
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (9)..(10)
<223> OTHER INFORMATION: thymidine 3'-O-phosphorothioate

<400> SEQUENCE: 30
ccaggagatt ccac                                                   14
```

```
<210> SEQ ID NO 31
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (2)..(2)
<223> OTHER INFORMATION: thymidine 3'-O-phosphorothioate
<220> FEATURE:
<221> NAME/KEY: modified_base
<222> LOCATION: (12)..(12)
<223> OTHER INFORMATION: thymidine 3'-O-phosphorothioate

<400> SEQUENCE: 31
gtggaatctc ctgg                                              14

<210> SEQ ID NO 32
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (7)..(7)
<223> OTHER INFORMATION: thymidine 3'-O-phosphorothioate
<220> FEATURE:
<221> NAME/KEY: modified_base
<222> LOCATION: (9)..(9)
<223> OTHER INFORMATION: thymidine 3'-O-phosphorothioate

<400> SEQUENCE: 32
gtggaatctc ctgg                                              14

<210> SEQ ID NO 33
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (2)..(2)
<223> OTHER INFORMATION: thymidine 3'-O-phosphorothioate
<220> FEATURE:
<221> NAME/KEY: modified_base
<222> LOCATION: (7)..(7)
<223> OTHER INFORMATION: thymidine 3'-O-phosphorothioate
<220> FEATURE:
<221> NAME/KEY: modified_base
<222> LOCATION: (9)..(9)
<223> OTHER INFORMATION: thymidine 3'-O-phosphorothioate
<220> FEATURE:
<221> NAME/KEY: modified_base
<222> LOCATION: (12)..(12)
<223> OTHER INFORMATION: thymidine 3'-O-phosphorothioate

<400> SEQUENCE: 33
gtggaatctc ctgg                                              14

<210> SEQ ID NO 34
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (2)..(2)
```

```
<223> OTHER INFORMATION: phosphorothioate or phosphorodithioate on
      complement strand
<220> FEATURE:
<221> NAME/KEY: modified_base
<222> LOCATION: (12)..(12)
<223> OTHER INFORMATION: phosphorothioate or phosphorodithioate on
      complement strand

<400> SEQUENCE: 34
ccaggagatt ccac                                                      14

<210> SEQ ID NO 35
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (5)..(5)
<223> OTHER INFORMATION: phosphorothioate or phosphorodithioate on
      complement strand
<220> FEATURE:
<221> NAME/KEY: modified_base
<222> LOCATION: (7)..(7)
<223> OTHER INFORMATION: phosphorothioate or phosphorodithioate on
      complement strand

<400> SEQUENCE: 35
ccaggagatt ccac                                                      14

<210> SEQ ID NO 36
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (2)..(2)
<223> OTHER INFORMATION: phosphorothioate or phosphorodithioate on
      complement strand
<220> FEATURE:
<221> NAME/KEY: modified_base
<222> LOCATION: (5)..(5)
<223> OTHER INFORMATION: phosphorothioate or phosphorodithioate on
      complement strand
<220> FEATURE:
<221> NAME/KEY: modified_base
<222> LOCATION: (7)..(7)
<223> OTHER INFORMATION: phosphorothioate or phosphorodithioate on
      complement strand
<220> FEATURE:
<221> NAME/KEY: modified_base
<222> LOCATION: (12)..(12)
<223> OTHER INFORMATION: phosphorothioate or phosphorodithioate on
      complement strand

<400> SEQUENCE: 36
ccaggagatt ccac                                                      14

<210> SEQ ID NO 37
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (9)..(10)
<223> OTHER INFORMATION: phosphorothioate or phosphorodithioate
<220> FEATURE:
<221> NAME/KEY: modified_base
```

```
<222> LOCATION: (2)..(2)
<223> OTHER INFORMATION: phosphorothioate or phosphorodithioate on
      complement strand
<220> FEATURE:
<221> NAME/KEY: modified_base
<222> LOCATION: (12)..(12)
<223> OTHER INFORMATION: phosphorothioate or phosphorodithioate on
      complement strand

<400> SEQUENCE: 37
ccaggagatt ccac                                                     14

<210> SEQ ID NO 38
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (9)..(10)
<223> OTHER INFORMATION: phosphorothioate or phosphorodithioate
<220> FEATURE:
<221> NAME/KEY: modified_base
<222> LOCATION: (5)..(5)
<223> OTHER INFORMATION: phosphorothioate or phosphorodithioate on
      complement strand
<220> FEATURE:
<221> NAME/KEY: modified_base
<222> LOCATION: (7)..(7)
<223> OTHER INFORMATION: phosphorothioate or phosphorodithioate on
      complement strand

<400> SEQUENCE: 38
ccaggagatt ccac                                                     14

<210> SEQ ID NO 39
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (9)..(10)
<223> OTHER INFORMATION: phosphorothioate or phosphorodithioate
<220> FEATURE:
<221> NAME/KEY: modified_base
<222> LOCATION: (2)..(2)
<223> OTHER INFORMATION: phosphorothioate or phosphorodithioate on
      complement strand
<220> FEATURE:
<221> NAME/KEY: modified_base
<222> LOCATION: (5)..(5)
<223> OTHER INFORMATION: phosphorothioate or phosphorodithioate on
      complement strand
<220> FEATURE:
<221> NAME/KEY: modified_base
<222> LOCATION: (7)..(7)
<223> OTHER INFORMATION: phosphorothioate or phosphorodithioate on
      complement strand
<220> FEATURE:
<221> NAME/KEY: modified_base
<222> LOCATION: (12)..(12)
<223> OTHER INFORMATION: phosphorothioate or phosphorodithioate on
      complement strand

<400> SEQUENCE: 39
ccaggagatt ccac                                                     14

<210> SEQ ID NO 40
<211> LENGTH: 22
<212> TYPE: DNA
```

```
<213> ORGANISM: Artificial Sequence
<220> FEATURE:
<223> OTHER INFORMATION: Aptamer

<400> SEQUENCE: 40
agttgagggg actttcccag gc                                                    22

<210> SEQ ID NO 41
<211> LENGTH: 33
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (9)..(9)
<223> OTHER INFORMATION: phosphate ester
<220> FEATURE:
<221> NAME/KEY: modified_base
<222> LOCATION: (9)..(9)
<223> OTHER INFORMATION: phosphorodithioate
<220> FEATURE:
<221> NAME/KEY: modified_base
<222> LOCATION: (20)..(20)
<223> OTHER INFORMATION: phosphorodithioate
<220> FEATURE:
<221> NAME/KEY: modified_base
<222> LOCATION: (20)..(20)
<223> OTHER INFORMATION: phosphate ester

<400> SEQUENCE: 41
ccaggagatt ccactttgt ggaatctcct gga                                         33

<210> SEQ ID NO 42
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (9)..(10)
<223> OTHER INFORMATION: phosphorothioate or phosphorodithioate

<400> SEQUENCE: 42
ccaggagatt ccac                                                             14

<210> SEQ ID NO 43
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (3)..(3)
<223> OTHER INFORMATION: phosphorothioate or phosphorodithioate
<220> FEATURE:
<221> NAME/KEY: modified_base
<222> LOCATION: (13)..(13)
<223> OTHER INFORMATION: phosphorothioate or phosphorodithioate

<400> SEQUENCE: 43
ccaggagatt ccac                                                             14

<210> SEQ ID NO 44
<211> LENGTH: 14
<212> TYPE: DNA
<213> ORGANISM: Artificial Sequence
<220> FEATURE:
<223> OTHER INFORMATION: Aptamer
```

```
<220> FEATURE:
<221> NAME/KEY: modified_base
<222> LOCATION: (6)..(6)
<223> OTHER INFORMATION: phosphorothioate or phosphorodithioate
<220> FEATURE:
<221> NAME/KEY: modified_base
<222> LOCATION: (8)..(8)
<223> OTHER INFORMATION: phosphorothioate or phosphorodithioate

<400> SEQUENCE: 44
ccaggagatt ccac                                                            14

<210> SEQ ID NO 45
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (6)..(6)
<223> OTHER INFORMATION: phosphorothioate or phosphorodithioate
<220> FEATURE:
<221> NAME/KEY: modified_base
<222> LOCATION: (3)..(3)
<223> OTHER INFORMATION: phosphorothioate or phosphorodithioate
<220> FEATURE:
<221> NAME/KEY: modified_base
<222> LOCATION: (8)..(8)
<223> OTHER INFORMATION: phosphorothioate or phosphorodithioate

<400> SEQUENCE: 45
ccaggagatt ccac                                                            14

<210> SEQ ID NO 46
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (8)..(8)
<223> OTHER INFORMATION: phosphorothioate or phosphorodithioate
<220> FEATURE:
<221> NAME/KEY: modified_base
<222> LOCATION: (6)..(6)
<223> OTHER INFORMATION: phosphorothioate or phosphorodithioate
<220> FEATURE:
<221> NAME/KEY: modified_base
<222> LOCATION: (13)..(13)
<223> OTHER INFORMATION: phosphorothioate or phosphorodithioate

<400> SEQUENCE: 46
ccaggagatt ccac                                                            14

<210> SEQ ID NO 47
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (8)..(8)
<223> OTHER INFORMATION: phosphorothioate or phosphorodithioate
<220> FEATURE:
<221> NAME/KEY: modified_base
<222> LOCATION: (3)..(3)
<223> OTHER INFORMATION: phosphorothioate or phosphorodithioate
<220> FEATURE:
<221> NAME/KEY: modified_base
<222> LOCATION: (6)..(6)
```

```
<223> OTHER INFORMATION: phosphorothioate or phosphorodithioate
<220> FEATURE:
<221> NAME/KEY: modified_base
<222> LOCATION: (13)..(13)
<223> OTHER INFORMATION: phosphorothioate or phosphorodithioate

<400> SEQUENCE: 47
ccaggagatt ccac                                                       14

<210> SEQ ID NO 48
<211> LENGTH: 14
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (3)..(3)
<223> OTHER INFORMATION: phosphorothioate or phosphorodithioate
<220> FEATURE:
<221> NAME/KEY: modified_base
<222> LOCATION: (4)..(4)
<223> OTHER INFORMATION: phosphorothioate or phosphorodithioate
<220> FEATURE:
<221> NAME/KEY: modified_base
<222> LOCATION: (9)..(10)
<223> OTHER INFORMATION: phosphorothioate or phosphorodithioate

<400> SEQUENCE: 48
ccaggagatt ccac                                                       14

<210> SEQ ID NO 49
<211> LENGTH: 22
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (12)..(12)
<223> OTHER INFORMATION: phosphorothioate or phosphorodithioate
<220> FEATURE:
<221> NAME/KEY: modified_base
<222> LOCATION: (14)..(14)
<223> OTHER INFORMATION: phosphorothioate or phosphorodithioate
<220> FEATURE:
<221> NAME/KEY: modified_base
<222> LOCATION: (18)..(18)
<223> OTHER INFORMATION: phosphorothioate or phosphorodithioate
<220> FEATURE:
<221> NAME/KEY: modified_base
<222> LOCATION: (13)..(13)
<223> OTHER INFORMATION: phosphorothioate or phosphorodithioate on
      complement strand
<220> FEATURE:
<221> NAME/KEY: modified_base
<222> LOCATION: (15)..(15)
<223> OTHER INFORMATION: phosphorothioate or phosphorodithioate on
      complement strand

<400> SEQUENCE: 49
ggggcggggg gatatggaca cc                                              22

<210> SEQ ID NO 50
<211> LENGTH: 22
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (16)..(16)
<223> OTHER INFORMATION: phosphorothioate or phosphorodithioate
```

```
<220> FEATURE:
<221> NAME/KEY: modified_base
<222> LOCATION: (14)..(14)
<223> OTHER INFORMATION: phosphorothioate or phosphorodithioate
<220> FEATURE:
<221> NAME/KEY: modified_base
<222> LOCATION: (5)..(5)
<223> OTHER INFORMATION: phosphorothioate or phosphorodithioate on
      complement strand
<220> FEATURE:
<221> NAME/KEY: modified_base
<222> LOCATION: (8)..(8)
<223> OTHER INFORMATION: phosphorothioate or phosphorodithioate on
      complement strand
<220> FEATURE:
<221> NAME/KEY: modified_base
<222> LOCATION: (10)..(10)
<223> OTHER INFORMATION: phosphorothioate or phosphorodithioate on
      complement strand
<220> FEATURE:
<221> NAME/KEY: modified_base
<222> LOCATION: (13)..(13)
<223> OTHER INFORMATION: phosphorothioate or phosphorodithioate on
      complement strand
<220> FEATURE:
<221> NAME/KEY: modified_base
<222> LOCATION: (18)..(18)
<223> OTHER INFORMATION: phosphorothioate or phosphorodithioate on
      complement strand

<400> SEQUENCE: 50
gggctggtgt ggtagactcc cc                                       22

<210> SEQ ID NO 51
<211> LENGTH: 22
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (8)..(8)
<223> OTHER INFORMATION: phosphorothioate or phosphorodithioate
<220> FEATURE:
<221> NAME/KEY: modified_base
<222> LOCATION: (10)..(10)
<223> OTHER INFORMATION: phosphorothioate or phosphorodithioate
<220> FEATURE:
<221> NAME/KEY: modified_base
<222> LOCATION: (12)..(12)
<223> OTHER INFORMATION: phosphorothioate or phosphorodithioate
<220> FEATURE:
<221> NAME/KEY: modified_base
<222> LOCATION: (14)..(14)
<223> OTHER INFORMATION: phosphorothioate or phosphorodithioate

<400> SEQUENCE: 51
cccgcccaca cacaccgccc cc                                       22

<210> SEQ ID NO 52
<211> LENGTH: 23
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (9)..(9)
<223> OTHER INFORMATION: phosphorothioate or phosphorodithioate
<220> FEATURE:
<221> NAME/KEY: modified_base
<222> LOCATION: (11)..(11)
<223> OTHER INFORMATION: phosphorothioate or phosphorodithioate
<220> FEATURE:
<221> NAME/KEY: modified_base
```

```
<222> LOCATION: (13)..(13)
<223> OTHER INFORMATION: phosphorothioate or phosphorodithioate
<220> FEATURE:
<221> NAME/KEY: modified_base
<222> LOCATION: (14)..(14)
<223> OTHER INFORMATION: phosphorothioate or phosphorodithioate
<220> FEATURE:
<221> NAME/KEY: modified_base
<222> LOCATION: (16)..(16)
<223> OTHER INFORMATION: phosphorothioate or phosphorodithioate
<220> FEATURE:
<221> NAME/KEY: modified_base
<222> LOCATION: (18)..(18)
<223> OTHER INFORMATION: phosphorothioate or phosphorodithioate
<220> FEATURE:
<221> NAME/KEY: modified_base
<222> LOCATION: (22)..(22
<223> OTHER INFORMATION: phosphorothioate or phosphorodithioate
<220> FEATURE:
<221> NAME/KEY: modified_base
<222> LOCATION: (17)..(17)
<223> OTHER INFORMATION: phosphorothioate or phosphorodithioate on
      complement strand

<400> SEQUENCE: 52
gggccgggag agaacatagc gac                                             23

<210> SEQ ID NO 53
<211> LENGTH: 22
<212> TYPE: DNA
<213> ORGANISM: Artificial Sequence
<220> FEATURE:
<223> OTHER INFORMATION: Aptamer
<220> FEATURE:
<221> NAME/KEY: misc_feature
<222> LOCATION: (4)..(4)
<223> OTHER INFORMATION: n = a, c, t, or g
<220> FEATURE:
<221> NAME/KEY: misc_feature
<222> LOCATION: (6)..(8)
<223> OTHER INFORMATION: n = a, c, t, or g
<220> FEATURE:
<221> NAME/KEY: modified_base
<222> LOCATION: (12)..(12)
<223> OTHER INFORMATION: phosphorothioate or phosphorodithioate
<220> FEATURE:
<221> NAME/KEY: modified_base
<222> LOCATION: (14)..(14)
<223> OTHER INFORMATION: phosphorothioate or phosphorodithioate
<220> FEATURE:
<221> NAME/KEY: modified_base
<222> LOCATION: (16)..(16)
<223> OTHER INFORMATION: phosphorothioate or phosphorodithioate

<400> SEQUENCE: 53
cccncnnnca cacaccgccc cc                                              22

<210> SEQ ID NO 54
<211> LENGTH: 22
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (6)..(6)
<223> OTHER INFORMATION: phosphorothioate or phosphorodithioate
<220> FEATURE:
<221> NAME/KEY: modified_base
<222> LOCATION: (4)..(4)
<223> OTHER INFORMATION: phosphorothioate or phosphorodithioate
<220> FEATURE:
<221> NAME/KEY: modified_base
<222> LOCATION: (3)..(3)
<223> OTHER INFORMATION: phosphorothioate or phosphorodithioate on
```

```
       complement strand
<220> FEATURE:
<221> NAME/KEY: modified_base
<222> LOCATION: (5)..(5)
<223> OTHER INFORMATION: phosphorothioate or phosphorodithioate on
      complement strand
<220> FEATURE:
<221> NAME/KEY: modified_base
<222> LOCATION: (8)..(8)
<223> OTHER INFORMATION: phosphorothioate or phosphorodithioate on
      complement strand
<220> FEATURE:
<221> NAME/KEY: modified_base
<222> LOCATION: (10)..(10)
<223> OTHER INFORMATION: phosphorothioate or phosphorodithioate on
      complement strand
<220> FEATURE:
<221> NAME/KEY: modified_base
<222> LOCATION: (18)..(18)
<223> OTHER INFORMATION: phosphorothioate or phosphorodithioate on
      complement strand

<400> SEQUENCE: 54
ggtatactct ccgcccctcc cc                                           22

<210> SEQ ID NO 55
<211> LENGTH: 26
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (4)..(4)
<223> OTHER INFORMATION: phosphorothioate or phosphorodithioate
<220> FEATURE:
<221> NAME/KEY: modified_base
<222> LOCATION: (6)..(6)
<223> OTHER INFORMATION: phosphorothioate or phosphorodithioate
<220> FEATURE:
<221> NAME/KEY: modified_base
<222> LOCATION: (10)..(10)
<223> OTHER INFORMATION: phosphorothioate or phosphorodithioate
<220> FEATURE:
<221> NAME/KEY: modified_base
<222> LOCATION: (12)..(12)
<223> OTHER INFORMATION: phosphorothioate or phosphorodithioate
<220> FEATURE:
<221> NAME/KEY: modified_base
<222> LOCATION: (7)..(7)
<223> OTHER INFORMATION: phosphorothioate or phosphorodithioate on
      complement strand
<220> FEATURE:
<221> NAME/KEY: modified_base
<222> LOCATION: (9)..(9)
<223> OTHER INFORMATION: phosphorothioate or phosphorodithioate on
      complement strand

<400> SEQUENCE: 55
cccacatgta cacgccgccc ccgccc                                       26

<210> SEQ ID NO 56
<211> LENGTH: 22
<212> TYPE: DNA
<213> ORGANISM: Artificial Sequence
<220> FEATURE:
<223> OTHER INFORMATION: Aptamer
<220> FEATURE:
<221> NAME/KEY: misc_feature
<222> LOCATION: (9)..(9)
<223> OTHER INFORMATION: n = a, c, t, or g
<220> FEATURE:
<221> NAME/KEY: misc_feature
<222> LOCATION: (14)..(14)
<223> OTHER INFORMATION: n = a, c, t, or g
```

-continued

```
<220> FEATURE:
<221> NAME/KEY: modified_base
<222> LOCATION: (4)..(4)
<223> OTHER INFORMATION: phosphorothioate or phosphorodithioate
<220> FEATURE:
<221> NAME/KEY: modified_base
<222> LOCATION: (6)..(6)
<223> OTHER INFORMATION: phosphorothioate or phosphorodithioate
<220> FEATURE:
<221> NAME/KEY: modified_base
<222> LOCATION: (10)..(10)
<223> OTHER INFORMATION: phosphorothioate or phosphorodithioate
<220> FEATURE:
<221> NAME/KEY: modified_base
<222> LOCATION: (12)..(12)
<223> OTHER INFORMATION: phosphorothioate or phosphorodithioate
<220> FEATURE:
<221> NAME/KEY: modified_base
<222> LOCATION: (7)..(7)
<223> OTHER INFORMATION: phosphorothioate or phosphorodithioate on
      complement strand

<400> SEQUENCE: 56
cccacatgna cacnccgccc cc                                          22

<210> SEQ ID NO 57
<211> LENGTH: 22
<212> TYPE: DNA
<213> ORGANISM: Artificial Sequence
<220> FEATURE:
<223> OTHER INFORMATION: Aptamer
<220> FEATURE:
<221> NAME/KEY: modified_base
<222> LOCATION: (7)..(7)
<223> OTHER INFORMATION: phosphorothioate or phosphorodithioate
<220> FEATURE:
<221> NAME/KEY: modified_base
<222> LOCATION: (9)..(9)
<223> OTHER INFORMATION: phosphorothioate or phosphorodithioate

<400> SEQUENCE: 57
gggcgtatat gtgtggcggg gg                                          22
```

THIO-MODIFIED APTAMER SYNTHETIC METHODS AND COMPOSITIONS

This is a continuation-in-part application claiming priority based on U.S. Provisional Application Ser. No. 60/105,600 filed Oct. 26, 1998.

Work resulting in the present invention was supported in part by United States Government grants DARPA 9624-107 FP, NIH AI27744, DARPA 3-14552-644101 and NIH 3-14546-477999. According, the U.S. Government has certain rights in the invention.

BACKGROUND OF THE INVENTION

Without limiting the scope of the invention, its background is described in connection with methods for the preparation of oligonucleotide "decoys".

Oligonucleotide agents have been shown to have functional activity in vitro and thus the promise of therapeutic potential. Some of these agents are believed to operate via mechanisms such as the sequence-specific antisense translation arrest of mRNA expression or through direct binding to protein targets where they function as "decoys". While oligonucleotide agents show therapeutic promise, various pharmacological problems must first be overcome.

Oligonucleotide agents have been used as high specificity therapeutic agents in vitro. High sensitivity to nuclease digestion, however, makes oligonucleotide agents unstable and thus impracticable for in vivo administration by either intravenous or oral routes.

From the foregoing it is apparent the there is a need in the art for methods for generating high binding, nuclease resistant oligonucleotide that retain their specifity. Also needed are compounds and methods that permit the generation of high binding, high specificity, nuclease resistant oligonucleotide agents that have an improved half-life and are target specific.

One target for oligonucleotide decoy targeting is the transcriptional activating factor NF-κB, which is activated by many factors that increase the inflammatory response. The activation of NF-κB leads to the coordinated expression of many genes that encode proteins such as cytokines, chemokines, adhesion molecules, etc., which amplify and perpetuate immune response. Because of its pivotal importance in immune function, NF-κB has been a desired target for new types of anti-inflammatory treatments. Current anti-inflammatory treatments such as glucocorticoids function at least in part through inhibition of NF-κB. Glucocorticoids, however, have endocrine and metabolic side effects when given systematically. Anti-oxidants represent another class of compounds that inhibit NF-κB activation. Currently available anti-oxidants, however, are relatively weak and have short-term effects. Aspirin and other salicylates also inhibit NF-κB, but only at relatively high concentrations that may have undesirable side effects. Naturally occurring inhibitors of NF-κB such as gliotoxin are potent and relatively specific, but also may have toxic effects.

NF-κB may have a particularly important role in the genesis of endotoxic shock, a disease entity of major clinical importance. In endotoxic shock, a series of intracellular signaling events, in which NF-κB activation figures importantly, lead to enhanced transcription of a variety of proinflammatory mediator genes, including tumor necrosis factor α, interleukin-1, inducible nitric oxide synthetase. These secreted mediators in turn lead to increased adhesion molecule expression on leukocytes and endothelial cells, increased tissue factor expression on monocytes and endothelial cells, promoting coagulation, vasodilation, capillary leakiness, and myocardial suppression. (Murphy, et al., *New Horizons* (1998) 6:181). Strong support for the role of NF-κB in septic shock in humans is afforded by the recent demonstration that sustained, increased NF-κB binding activity in nuclei of peripheral blood monocytes from septic patients predicted mortality.

From the foregoing it is apparent the there is a need in the art for methods for generating high binding, nuclease resistant aptamers that retained their specificity.

SUMMARY OF THE INVENTION

Aptamers may be defined as nucleic acid molecules that have been selected from random or unmodified oligonucleotides ("ODN") libraries by their ability to bind to specific targets or "ligands". An iterative process of in vitro selection may be used to enrich the library for species with high affinity to the target. The process involves repetitive cycles of incubation of the library with a desired target, separation of free oligonucleotides from those bound to the target and amplification of the bound ODN subset using the polymerase chain reaction ("PCR"). The penultimate result is a sub-population of sequences having high affinity for the target. The sub-population may then be subcloned to sample and preserve the selected DNA sequences. These "lead compounds" are studied in further detail to elucidate the mechanism of interaction with the target.

Modulation of the functional attributes of bioactive targets are achieved by aptamer binding. Binding may, for example, interrupt protein-DNA interactions such as those that occur between transcription factors and DNA in the process of gene activation. The ability to effectively modulate the effects of certain pluripotent transcription factors in vivo would provide a particularly valuable therapeutic tool.

NF-κB is a transcription factor whose activity plays a role in many disease processes and is thus an potential target for therapeutic control of gene expression. Aptamers can demonstrate high specificity in vitro for target proteins and may serve as therapeutics. High sensitivity to nuclease digestion makes unmodified aptamers unstable in complex biological systems and tehrefore, unable to mediate the effects of transcriptional factors such as NF-κB in vivo. Nuclease resistance is particularly important for the administration of nucleic acid-based therapeutics by either intravenous or oral routes. The present inventors recognized the need for new concepts in aptamer design that would permit the generation of effective nuclease resist aptamers and that such aptamers, if they could be developed, might serve as selective mediators of NF-κB activity.

Modification of oligonucleotides such as by thiolation of the phosphoryl oxygens of the ODNs can confer nuclease resistance. Thus, it has been shown by Gorenstein (Farschtschi, N. and Gorenstein, D. G., *Tetrahedron Lett.* (1988) 29:6843) and others (See e.g. Nielsen, et al., *Tetrahedron Lett.* (1988) 29:291) that sulfur-containing phosphorothioate and phosphorodithioate substituted oligonucleotides show reduced nuclease susceptibility.

Although phosphoromonothioate analogues ([S]-ODNs) are relatively nuclease resistant, due to the new chiral phosphorus center, phosphoromonothioate mixtures are diasteromeric and thus have variable biochemical, biophysical and biological properties. While stereocontrolled synthesis of P-chiral [S]-ODNs (Yang, et al., *J. Bioorganic & Med. Chem. Lett.* (1997) 7:2651) represents one possible solution to this problem, another lies in the synthesis of modifications that are achiral at phosphorus.

In contrast to the phosphomonothioates, the dithioates ([S$_2$]-ODN) contain an internucleotide phosphodiester group with sulfur substituted for both nonlinking phosphoryl oxygens, and are therefore both isosteric and isopolar with the normal phosphodiester link. Phosphodithioate analogues ([S$_2$]-ODNs) have been synthesized (Gorenstein, et al., U.S. Pat. No. 5,218,088) which have been shown to be highly nuclease resistant and effective as antisense agents. (Nielsen, et al., *Tetrahedron Lett.* (1988) 29:2911; Farschtschi and Gorenstein, *Tetrahedron Lett.* (1988) 29:6843). In contrast to the phosphoramidite-synthesized monothiophosphate [S]-ODNs, the dithioate [S$_2$]-ODNs are achiral about the dithiophosphate center, so problems associated with diastereomeric mixtures are completely avoided. The [S$_2$]-ODNs, like the [S]-ODNs, are taken up efficiently by cells.

It has been generally observed that the increased thioation of the phosphoryl oxygens of ODNs often leads to their enhanced binding to numerous proteins. For example, single-stranded [S$_2$]-ODNs are 36–600 times more effective in inhibiting HIV reverse transcriptase than normal antisense ODN or the [S]-ODN (Caruthers, M. H., *Abstract, In Oligonucleotides As Antisense Inhibitors of Gene Expression*, Rockville Md., Jun. 18–21, 1989).

It has also been noted, however, that oligonucleotides possessing high monothio- or dithio-phosphate backbone substitutions appear to be "stickier" towards proteins than normal phosphate esters, possibly based on the charge characteristics of the sulfonated nucleotides. The increased stickiness of thiolated ODNs results in loss of specificity, thus, defeating the promise of specific targeting offered by aptamer technology. Loss of specificity is critical in DNA binding proteins-DNA interactions, because most of the direct contacts between the proteins and their DNA binding sites are to the phosphate groups. As a further complication, it has been found that certain thiosubstitution can lead to structural perturbations in the structure of the duplex (Cho, et al., *J. Biomol. Struct. Dyn.* (1993) 11, 685–702).

In one embodiment of the present invention provides a novel application of DNA polymerase to incorporate chiral phosphorothioates and replicate a random sequence library simultaneously in order to prepare achiral NF-κB specific aptamers. A random phosphodiester oligonucleotide combinatorial library is synthesized wherein constituent oligonucleotides comprise at least a set of 5' and 3' PCR primer nucleotide sequences flanking a randomized nucleotide sequence. The library is amplified enzymatically using a mix of four nucleotide substrates, wherein at least a portion of the total quantity of at least one but no more than three of the nucleotides is modified, to form a modified oligonucleotide combinatorial library.

Furthermore, only a portion of the total quantity of given a nucleotide base may be modified and/or more than one modified nucleotide base is included in the amplification mix, thereby increasing the number of potential substitution. The modified oligonucleotide combinatorial library is next contacted or mixed with a target protein, e.g., an NF-kB dimer or constituent subunit protein, and the subset of oligonucleotides binding to the protein is isolated. The subset of NF-kB binding oligonucleotides is again amplified enzymatically using the mix of four nucleotide substrates, including modified nucleotides to form a modified oligonucleotide sub-library. The amplification and isolation steps are repeated iteratively until at least one aptamer having one or more modified oligonucleotides of defined sequence is obtained.

The unique chemical diversity of the oligonucleotide libraries generated by methodologies provided herein stems from both the nucleotide base-sequence and phosphorothioate backbone sequence. The present method provides achiral oligonucleotide products whether the amplification substrates are monothiophosphates or dithiophosphates. The present thioaptamer methodology provides compounds that are an improvement over existing antisense or "decoy" oligonucleotides because of their stereochemical purity. Chemically synthesized phosphorothioates may be a diastereomeric mixture with $2^n$ stereoisomers with n being the number of nucleotides in the molecule. These preparations are unsuitable for use in humans because only a small fraction of the stereoisomers will have useful activity and the remaining could have potential adverse effects. In contrast, enzymatically synthesized oligonucleotides are stereochemically pure due to the chirality of polymerase active sites. Inversion of configuration is believed to proceed from $R_p$ to $S_p$ during incorporation of dNMPαS into the DNA chain. The present dithiophosphate aptamers are free from diastereomeric mixtures.

The present inventors recognized that it is not possible to simply replace thiophosphates in a sequence that was selected for binding with a normal phosphate ester backbone oligonucleotide. Simple substitution was not practicable because the thiophosphates can significantly decrease (or increase) the specificity and/or affinity of the selected ligand for the target. It was also recognized that thiosubstitution leads to a dramatic change in the structure of the aptamer and hence alter its overall binding affinity. The sequences that were thioselected according to the present methodology, using as examples of DNA binding proteins both NF-IL6 and NF-κB, were different from those obtained by normal phosphate ester combinatorial selection.

The present invention takes advantage of the "stickiness" of thio- and dithio-phosphate ODN agents to enhance the affinity and specificity to a protein target. In a significant improvement over existing technology, the method of selection concurrently controls and optimizes the total number of thiolated phosphates to decrease non-specific binding to non-target proteins and to enhance only the specific favorable interactions with the target. The present invention permits control over that phosphates to be thio-substituted in a specific DNA sequence, thereby permitting the selective development of aptamers that have the combined attributes of affinity, specificity and nuclease resistance.

In one embodiment of the present invention, a method of post-selection aptamer modification is provided in which the therapeutic potential of the aptamer is improved by selective substitution of modified nucleotides into the aptamer oligonucleotide sequence. A target binding aptamer is identified and the nucleotide base sequence determined. Modified achiral nucleotides are substituted for one or more selected nucleotides in the sequence. In one embodiment, the substitution is obtained by chemical synthesis using dithiophosphate nucleotides. The resulting aptamers have the same nucleotide base sequence as the original aptamer but by virtue of the inclusion of modified nucleotides into selected locations in the sequences improved nuclease resistance is obtained.

Using the method disclosed hereinbelow, a family of aptamers with modifications at different locations was created and the binding efficiency for the target determined. Using the disclosed method, specific NF-κB binding aptamers were created that are not only more nuclease resistant but have increasing binding affinity over unmodified aptamers of the same sequence. In contrast to fully thiolated aptamers of the same sequence, the selectively thiolated aptamers of the present invention had greater selectivity for the desired target NF-κB dimers.

In one embodiment of the present invention, a process for fractionating oligonucleotides with varying degrees of thioation is provided. A crude oligonucleotide mixture is dissolved in a starting solvent, e.g., water. The dissolved oligonucleotide is loaded onto an anion-exchange column, e.g., an FPLC of HPLC Mono Q column. Oligonucleotides with varying degrees of thioation are sequentially eluted with a buffered salt gradient. In addition to the fractionation and collection of specific thiolation species, the method permits the ready removal of undesired monothiophosphate contaminates.

The controlled thiolation methodology of the present invention is applicable to the design of specific, nuclease resistant aptamers to virtually any target including without limitation amino acids, peptides, polypeptides (proteins), glycoproteins, carbohydrates, nucleotides and derivatives thereof, cofactors, antibiotics, toxins, and small organic molecules including inter alia, dyes, theophylline, and dopamine. It is contemplated, and within the scope of this invention, that the instant thioaptamers encompass further modifications to increase stability and specificity including for example disulfide crosslinking. It is further contemplated and within the scope of this invention that the instant thioaptamers encompass further modifications including, e.g., radiolabeling and/or conjugation with reporter groups, such as biotin or fluorescein, or other functional groups for use in in vitro and in vivo diagnostics and therapeutics.

The present invention further provides the application of this methodology to the generation of novel thiolated aptamers specific for nuclear factors such as, e.g., NF-IL6 and NF-κB. The NF-κB/Rel transcription factors are key mediators of immune and acute phase responses, apoptosis, cell proliferation and differentiation. The NF-κB/Rel transcription factors are also key transactivators acting on a multitude of human and pathogen genes, including HIV-1.

Several family members of NF-κB/Rel have been identified based not only on sequence, but also structural and functional homology. Members of this protein family are divided into two groups based on differences in structures, functions and modes of synthesis: one group includes of the precursor proteins p105 and p100 with ankyrin repeat domains in their carboxyl termini. Proteolytic processing removes the carboxyl halves to yield the mature forms p50 and p52, respectively. The subsequent homodimers are weak transcriptional activators at best, since they lack carboxyl transactivation domains. A second group, including p65 (RelA), c-Rel, v-Rel, Rel B, Dorsal, and Dif are not synthesized as precursors and are sequestered in the cytoplasm by association with inhibitors (IκB) or precursor proteins (p100 and p105). Homo- or hetero-dimers including at least one member from this group are strong transcriptional activators.

Both groups of NF-κB/Rel proteins can form homo- and hetero-dimers. Hetero-dimers consisting of p50 and p65 (RelA) are the ubiquitously expressed form of the NF-κB transcription factor. Upon nuclear entry, NF-κB/Rel proteins bind to specific sites resembling the consensus sequence, GGGRNNT(Y)CC. These sites are found in promoters and enhancers of a variety of cellular genes including genes involved in the immune response (IgκB, IL-2, IL-2Rα, cyclooxygenase-2), acute phase response genes (TNFα, IL-1, IL-6, TNFβ), viruses (HIV, CMV, SV-40), growth control proteins (p53, c-myc, ras, GM-CSF), NF-κB/Rel and IκB proteins and cell adhesion molecules (I-CAM, V-CAM and E-selectin) and many other genes. The affinity of the NF-κB/Rel proteins for DNA is determined by the sequence of the binding site. Different combinations of NF-κB/Rel proteins in dimers influence binding site preferences and affinities. Therefore, it is likely that different forms of NF-κB activate different sets of target genes with respect to certain NF-κB binding sites.

The present invention provides an aptamer capable of discriminating between, and binding to, a single NF-κB/Rel protein dimer species. Prior art backbone aptamers or target site sequences or fully monothiophosphate sequences bind to multiple proteins in cell culture. The present invention provides for both NF-IL6 and NF-κB, aptamers that are long enough to permit interaction with multiple proteins and provides methods to specifically select multi-protein complexes and to discriminate among the different transcription factors.

The present structure-based dithiophosphate and combinatorial monothiophosphate selection system provides for the identification of aptamers that have high specificity, and high affinity for DNA binding proteins, e.g, a single NF-κB heterodimer, in a cellular extract. The present invention encompasses the development of separate aptamers targeting any one of the 15 possible combinations of 5 homo- and hetero-dimers of the 5 different forms of NF-κB/Rel.

The present invention discloses the use of NF-κB dithioate aptamers to selectively bind various NF-κB hetero- and homo-dimers to down-regulate the pathogenic aspects of systemic inflammation and/or up-regulate the protective/anti-inflammatory aspects of the response and thus to protect against endotoxic shock and LPS tolerance.

NF-κB is activated by many factors that increase the immune response. NF-κB activation leads to the coordinated expression of many genes that encode proteins such as cytokines, chemokines, adhesion molecules, etc. all amplifying and perpetuating the immune response. In addition there is evidence that X-rays (used in treatment of Kaposi's sarcoma) are potent inducers of NF-κB, triggering HIV proviral transcription. (Faure, et al., *AIDS Research & Human Retroviruses* (1996) 12, 1519–1527). The NF-κB specific thioaptamers of the present invention provide for a generation of anti-AIDS therapeutics with specific application during the treatment of patients with Kaposi's sarcoma.

Alternatively, the present invention discloses the use of NF-κB specific thioaptamers targeted to p50.p50 or p52.p52 (inhibitors of NF-κB transactivation) to activate κB-specific gene expression (Zhang, et al., *Blood* (1998) 91:4136) and aid in "smoking out" latent reservoirs of HIV by inducing expression of latent virus infected cells that are then susceptible to combination anti-viral therapy.

The NF-κB aptamers of the present invention have utility in the study and treatment of the many diseases in which this transcription factor plays a critical role in gene activation, especially acute phase response and inflammatory response. These diseases include (but are not limited to): bacterial pathogenesis (toxic shock, sepsis), rheumatoid arthritis, Crohn's disease, generalized inflammatory bowel disease, asbestos lung diseases, Hodgkin's disease, prostrate cancer, ventilator induced lung injury, general cancer, AIDS, human cutaneous T cell lymphoma, lymphoid malignancies, HTLV-1 induced adult T-cell leukemia, atherosclerosis, cytomegalovirus, herpes simplex virus, JCV, SV-40, rhinovirus, influenza, neurological disorders, and lymphomas.

Another aspect of the present invention is to both thioselect and design aptamers (monothiophosphate and dithiophosphate, as well as other backbone substitutions) that specifically target protein.protein complexes such as the "enhanceosome". As part of the present invention, enhanced aptamer selectivity and binding has been achieved respective to protein.protein contacts as well as protein-aptamer contacts. Thiolated aptamers allow the formation of a specific protein.protein.aptamer complex capable of preferentially forming an inactive enhanceosome on a gene that is unable to interact with the basal transcriptional factors. Using the disclosed method and compositions, aptamers may be designed or selected that are specific for the multi-protein enhanceosome complex but not for the complete transcriptional activation complex.

The aptamers themselves have utility as biochemical research tools or medical diagnostics agents in cell culture, animal systems, in vitro systems and even to facilitate hot start PCR through the inhibition of high temperature polymerases. Three dimensional structural determination of modified aptamers with both high binding efficiency and specificity according to the present invention also provides a vehicle for drug design structural modeling of the active sites of desired drug targets.

The invention contemplates the use of PCR to incorporate up to three dNTPαSs into DNA. Incorporation of dNTPαSs is important because greater substitution may impart greater nuclease resistance to the thiolated aptamers. The use of dNTPαSs is also important because the initial library will also have greater diversity. Using the present invention thiolated aptamers may be selected having one or more thio-modified nucleotide substitutions.

Single-stranded nucleic acids are also known to exhibit unique structures. The best documented single-stranded nucleic acids structures are of single-stranded RNA. Single-stranded DNA can also adopt unique structures. The present invention is applicable to the selection of single-stranded phosphorothioate aptamers comprised of either RNA or DNA. Such single-stranded aptamers are applicable to both DNA (i.e., cell surface receptors, cytokines, etc.) and non-DNA binding proteins.

It is contemplated that the present methods and procedures may be scaled-up as would be necessary for high throughput thioaptamer screening and selection. For example, 96 well microtiter plates may be used to select aptamers to a number of different proteins under numerous conditions.

This technology is directly applicable to protein/DNA chip technology according to methodologies, e.g., those described in U.S. Pat. No. 5,874,219 incorporated herein by reference. By attaching the highly selective aptamers to a support, protein/DNA chip permits the identification and quantitation of the protein levels of all possible forms of not only NF-κB/Rel proteins but many other transcription factors and other proteins that function by forming different protein.protein complexes (i.e. NF-IL6/Lip/NF-κB, Bad/Bax/BCL-$X_S$/BCL-$X_L$, etc.). A 2D-arrayed chip would be capable of discriminating among 100's or even 1000's of protein.protein complexes in the cell simultaneously. The present invention discloses the attachment of nucleic acids, rather than unstable proteins, to the chip substrates, permitting current DNA chip technologies (photolithography, ink jet, etc.) may be used. Solid state chip technology provides structure-based and combinatorial drug design program as well as general medical diagnostics, making it feasible to monitor the varying populations of different protein.protein complexes resulting from disease progression or drug treatment.

BRIEF DESCRIPTION OF THE DRAWINGS

For a more complete understanding of the present invention, including features and advantages, reference is now made to the detailed description of the invention along with the accompanying figures:

FIG. 7a shows the sequences of thioselected NF-kB aptamers according to the present invention while;

FIG. 7b shows a consensus sequence determined therefrom;

DETAILED DESCRIPTION OF THE INVENTION

Figure 1:
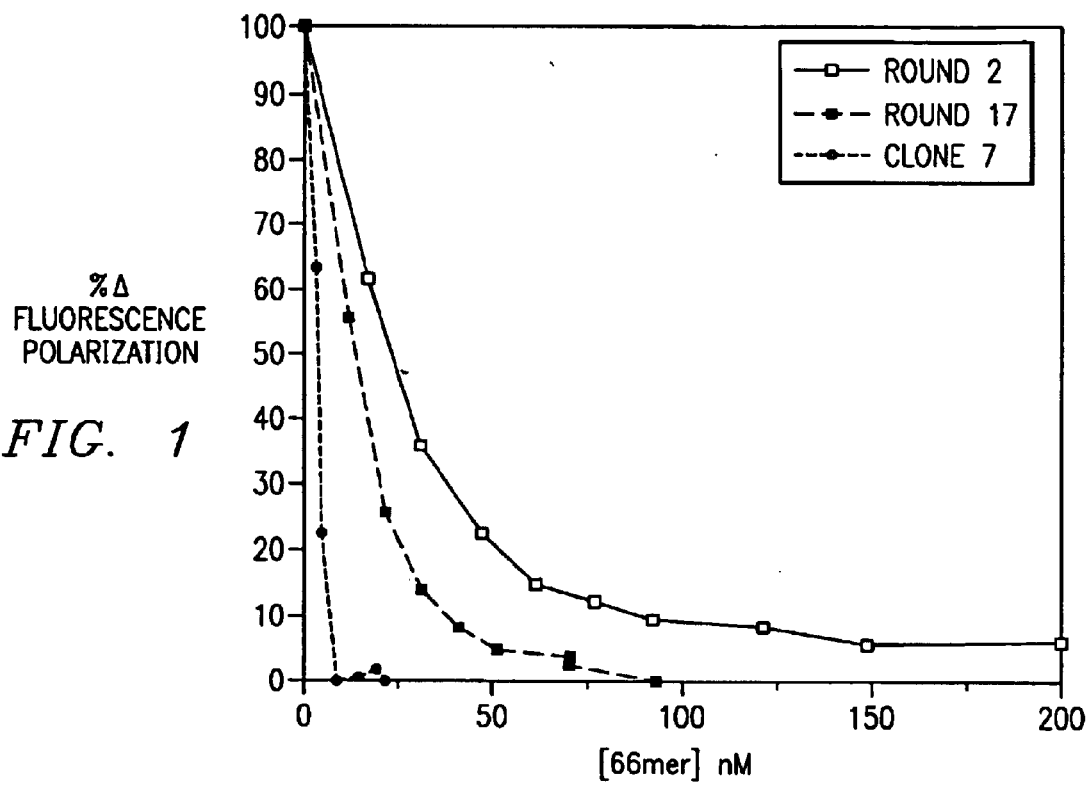
FIG. 1 depicts a competitive fluorescence polarization titration of 5'-labeled fluorescein-20-mer duplex/NF-IL6 TCD dimer complex.

While the making and using of various embodiments of the present invention are discussed in detail below, it should be appreciated that the present invention provides many applicable inventive concepts which can be employed in a wide variety of specific contexts. The specific embodiment discussed herein are merely illustrative of specific ways to make and use the invention and do not delimit the scope of the invention.

ABBREVIATIONS

The following abbreviations are used throughout this application:

bZIP—basic leucine zipper
BSA—bovine serum albumin
CD—circular dichroism
C/EBPβ—CCAAT-enhancer binding protein β
DNase 1—Deoxyribonuclease 1
DTT—dithiothreitol
EDTA—ethylene diamine tetraacetic acid
Il6—Interleukin-6 kb—kilobase (pairs)
kD—kilodalton
$K_{obs}$—observed binding constant
ODN—oligonucleotide
NMR—nuclear magnetic resonance
NF-KB—nuclear factor-κB
NF-IL6—nuclear factor for human IL6
dNTP(αS)—dNTP with monothiophosphorylation of the αphosphate of the tripolyphosphate
OD—optical density
PAGE—polyacrylamide gel electrophoresis
PCR—polymerase chain reaction
RT—reverse transcriptase
Taq—*Thermus aquaticus* DNA polymerase
TCD—tryptic core domain of NF-IL6
Tf—transcription factor To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "synthesizing" of a random combinatorial library refers to chemical methods known in the art of generating a desired sequence of nucleotides including where the desired sequence is random. Typically in the art, such sequences are produced in automated DNA synthesizers programed to the desired sequence. Such programing can include combinations of defined sequences and random nucleotides.

"Random combinatorial oligonucleotide library" means a large number of oligonucleotides of different sequence where the insertion of a given base at given place in the sequence is random.

"PCR primer nucleotide sequence" refers to a defined sequence of nucleotides forming an oligonucleotide which is used to anneal to a homologous or closely related sequence in order form the double strand required to initiate elongation using a polymerase enzyme.

"Amplifying" means duplicating a sequence one or more times. Relative to a library, amplifying refers to en masse duplication of at least a majority of individual members of the library.

As used herein, "thiophosphosphate" or "phosphorothioate" are used interchangeably to refer analogues of DNA or RNA having sulphur in place of oxygen as one of the non-bridging ligands bound to the phosphorus. Monothiophosphates [αS] have one sulfur and are thus chiral around the phosphorus center. Dithiophosphates are substituted at both oxygens and are thus achiral. Phosphorothioate nucleotides are commercially available or can be synthesized by several different methods known in the art.

"Modified" means oligonucleotides or libraries comprising oligonucleotides wherein one or more of the four constituent nucleotide bases are analogues or esters of nucleotides normally comprising DNA or RNA backbones and wherein such modification confers increased nuclease resistance. Thiophosphosphate nucleotides are an example of modified nucleotides.

"Phosphodiester oligonucleotide" means a chemically normal (unmodified) RNA or DNA oligonucleotide.

Amplifying "enzymatically" refers to duplication of the oligonucleotide using a nucleotide polymerase enzyme such as DNA or RNA polymerase. Where amplification employs repetitive cycles of duplication such as using the "polymerase chain reaction", the polymerase is a heat stable polymerase such as the DNA polymerase of *Thermus aquaticus*.

"Contacting" in the context of target selection means incubating a oligonucleotide library with target molecules.

"Target molecule" means any molecule to which specific aptamer selection is desired.

"Essentially homologous" means containing at least either the identified sequence or the identified sequence with one nucleotide substitution.

"Isolating" in the context of target selection means separation of oligonucleotide/target complexes, preferably DNA/protein complexes, under conditions in which weak binding oligonucleotides are eliminated. In one preferred embodiment DNA/protein complexes are retained on a filter through which non-binding oligonucleotides are washed.

By "split synthesis" it is meant that each unique member of the combinatorial library is attached to a separate support bead on a two column DNA synthesizer, a different thiophosphoramidite is first added onto both identical supports (at the appropriate sequence position) on each column. After the normal cycle of oxidation and blocking (which introduces the dithiophosphate linkage at this position), the support beads are removed from the columns, mixed together and the mixture reintroduced into both columns. Synthesis may proceed with further iterations of mixing or with distinct nucleotide addition.

A recent advance in combinatorial chemistry has been the ability to construct and screen large random sequence nucleic acid libraries for affinity to proteins (Gold et al., *Proc. Natl. Acad. Sci. U.S.A.* (1997) 94: 59; Tian et al., *RNA* (1995) 1: 317; Ekland et al., *Science* (1995) 269: 364). The nucleic acid libraries are usually selected by incubating the target protein with the library and then employing a method of separating the non-binding species from the bound. The bound fractions are then amplified using PCR and subsequently incubated again with the protein for a second round of the screening or selection process. These iterations are repeated until the library is enhanced for sequences having high affinity for the target protein.

Agents selected from combinatorial libraries of RNA and DNA in the past have normal phosphate ester backbones and thus are generally unsuitable as drugs in vivo because of their nuclease susceptibility. Although varying degrees of nuclease resistance may be obtained using modified nucleotides, for example, by thiosubstitution at the non-binding oxygen groups of the phosphate backbone, the present inventors recognized that the functional effect of substitution of nuclease resistant thiophosphates could not be predicted since the sulfur substitution may lead to either decreased or increased binding to a specific protein.

The present inventors developed a novel combinatorial approach involving the construction and screening of a phosphorothioate DNA library. In one embodiment, the target selected was the nuclear factor for IL6 (NF-IL6), a basic leucine zipper transcription factor involved in the induction of acute-phase responsive and cytokine gene promoters in response to inflammation (Akira & Kishimoto, *Immun. Rev.* (1992) 127:25).

The following examples are include for the sake of completeness of disclosure and to illustrate the methods of making the compositions and composites of the present invention as well as to present certain characteristics of the compositions. In no way are these examples intended to limit the scope or teaching of this disclosure.

EXAMPLE 1

Thioselection of Phosphorodithioate Aptamers Binding to NF-IL6

The present invention provides oligonucleotide combinatorial methods that may be extended to selection not only of base sequence but of phosphate (or monothiophosphate) backbones as well. The best monothiophosphate aptamers were obtained using the following method. As an example, binding was increased at least 5-fold to the NF-IL6 tryptic core domain (TCD) than the normal backbone sequence. The sequences selected, while related to the normal backbone CAAC/T half-sites (for Family B below), show distinct differences that are likely attributable to alterations in the nature of the protein-phosphate backbone interactions in the complex.

Because Taq polymerase can use up to 3 different dNTP (αS)s in the polymerization reaction, further backbone substitutions are possible. The present invention contemplates the incorporation of both triphosphate and triphosphate(αS) nucleotides in the PCR mix so that a library of both phosphate and monothiophosphate backbones may be randomized at the same base position, greatly increasing the diversity of the library.

A. Library Generation

A random combinatorial library of normal phosphoryl backbone oligonucleotides was synthesized by automated DNA synthesis (Midland Certified Reagents, Midland, Tex.) programmed to include all 4 monomer bases of the oligonucleotide during the coupling of residues in a randomized segment. This synthetic library has PCR primer segments at the 5' and 3' ends flanking the randomized region and thus can be replicated and amplified by Taq DNA polymerase (AMPLITAQ, Perkin Elmer). A 66-mer has been used with a 22 base pair random central segment flanked by 21 and 23 base pair PCR primer regions:

5'CAGTGCTCTAGAGGATCCGTGACN$_{22}$CGAAG CTTATC-
GATCCGAGCG3' (SEQ ID NO.:1)

The resulting library thus exists as a population with potentially $4^{22}$ ($10^{13}$) different sequences. The oligonucleotide library with phosphorothioate backbone substituted at dA positions was then synthesized by PCR amplification of the 66-mer template using commercially available Taq polymerase and a mix of dATP(αS), dTTP, dGTP and dCTP as substrates (Pharmacia, Inc.). The PCR amplification of the starting random library included: 40 μM each of dATP(αS), dTTP, dGTP and dCTP, 500 μM MgCl$_2$, 2.9 μM 66mer random template, 5 U Taq polymerase and 400 nM each primer in a total volume of 100 μL. PCR was run for 25 cycles of 95° C./1 min, 72° C./1 min. This polymerase is known to PCR amplify a phosphorothioate backbone template (Nakamaye et al. Nucl. Acids Res.(1988) 16: 9947) so long as the dNTP(αS)'s are limited to no more than 3 different bases in the mixture (Ciafre et al. Nucl. Acids Res.(1995) 23:4134). It also acts stereospecifically to incorporate the $S_p$-diastereomers of dNTP(αS)'s and is believed to yield the $R_p$ stereoisomer as is found for other polymerases (Eckstein, F. Ann. Rev. Biochem.(1985) 54: 367).

B. NF-IL6 Preparation

When full length NF-IL6 complexed with DNA is exposed to trypsin, a 9.5 kDa fragment is identified as the smallest fragment stably resistant to proteolysis. This basic leucine zipper (bZIP) domain peptide spans amino acids $A^{266}$-$C^{345}{}_1$, and is termed the NF-IL6 tryptic core domain (TCD).

High level expression of recombinant NF-IL6 bZIP region in E. coli was achieved in the T7 promoter/polymerase system. The TCD expressed as a nonfusion protein constitutes 30% of the total soluble E. coli protein and was purified as previously described (Brasier, et al., J. Biol. Chem. (1994) 269: 1034). The TCD bZIP domain binds DNA in a manner indistinguishable from full length NF-IL6. Electrospray mass spectrometry indicates that the mass of TCD is 18,926 Da. These data indicated that TCD is a covalently linked dimer through its C-terminal disulfide bond. The present selection, however, was performed under conditions in which the disulfides are reduced and the TCD exists as a non-covalent dimer.

C. NF-IL6 Thiophosphate selection

The random library was screened to determine sequences that have affinity to the bZIP domain of NF-IL6. PCR amplification of the single stranded library provided chiral duplex phosphorothioate 66-mer at all dA positions (except for the primer segments). A filter-binding method was used for enrichment of binding sites, although other methods' known in the art are also suitable. The PCR amplified random library of the chiral duplex phosphorothioate 66-mer at dA positions (100 pmols) was incubated with 6.6 pmols TCD in 50 μl buffer containing 10 mM Tris, pH 7.5, 1 mM DTT and 50 to 400 mM KCl and filtered through Millipore HAWP25 mm nitrocellulose filters (following a modification of the protocol from Thiesen et al., Nucl. Acids Res. (1990) 18: 3203). The filters had been previously presoaked in 1×binding buffer that contains no protein or DNA (10 mM Tris, pH 7.5, 1 mM DTT and 50 to 400 mM KCl). Under these conditions the DNA/protein complexes were retained on the filter. The filter was then washed with 10 ml of 1×binding buffer to remove the majority of the DNA that only weakly bound to the protein.

A 1 ml solution of 8 M urea and 4 M NaCl was then added to elute the protein-bound DNA. A negative control without protein was performed simultaneously to monitor any non-specific binding of the thiophosphate DNA library to the nitrocellulose filter. DNA was ethanol precipitated and once again PCR amplified with the dATP(αS) nucleotide mix. The PCR thermal profile was different than that used to make the starting library: 95° C./1 min, 55° C./1 min, 68° C./1 min for 25 cycles. The PCR products were analyzed by 15% non-denaturing polyacrylamide gel electrophoresis.

At various stages of the selection process the resulting libraries were cloned and plasmids from individual colonies sequenced. The normal phosphate ester 66-mer duplexes in the libraries were sub-cloned using the TA cloning kit (Invitrogen). As a control, four clones were also sequenced from the original combinatorial library and shown to have random sequence.

The present invention provides a thiophosphate backbone combinatorial library created by PCR methods with substitution of appropriate dNTP(αS) in the Taq polymerization step. This combinatorial thiophosphate duplex library was successfully screened for binding to the TCD of NF-IL6 by a filter binding method that was modified to minimize non-specific binding of the thiophosphate oligonucleotides to the nitrocellulose filter. The thiophosphate substituted DNA may be eluted from the filter using, e.g., high salt, protein denaturing conditions described or other conditions known in the art. Subsequent ethanol precipitation and another PCR thiophosphate amplification provide product pools for additional rounds of selection may also be used to further select for high affinity binding. In order to increase the stringency of binding of the remaining pool of DNA in the library (thereby, selecting tighter binding members of the library), the KCl concentration was increased in subsequent rounds from 50 to 400 mM. The stringency of selection was also manipulated by lowering the amount of protein as the iteration number increased.

| "GC-box" | Duplex format |
|---|---|
| "5'ACAGC.GCTGT" | 5' ACAGC<br>TGTCG 5' |
| "5'ACATG.CATGT" | 5' ACATG<br>TGTAC 5' |
| "5'ACACG.CGTGT" | 5' ACACG<br>TGTGC 5' |

Nascent elements of this new variation were also observed at round 7 of the first selection(GC box, ACA and ACACG units).

TABLE I

Sequences of Variable 22-mer Region in 66-mer Thiophosphate Aptamers, Selected after Indicated Rounds.*

| CONSENSUS | GC-box | ACAGC.GCTGT | ACATG.CATGT | ACACG.CGTGT |
|---|---|---|---|---|
| 1st INDEPENDENT SELECTION STUDY, ROUND 7 | | | | |
| 1 (SEQ ID No.:2) | 5'd GCC | GTCC | ACATA C G | ACACACC |
| 2 (SEQ ID No.:3) | 5'dGGCC | GACCGC | ACA G C | ACAACCC |
| 3 (SEQ ID No.:4) | 5'dGGC | GCGGAT | ACAAC C C | ACACGC |
| 2nd INDEPENDENT SELECTION STUDY, ROUND 10 | | | | |
| 4 (SEQ ID No.:5) | 5'dGGGCCC | GCTGT | ACATG C | ACACG |
| 5 (SEQ ID No.:5) | 5'dGGGCCC | GCTGT | ACATG C | ACACG |
| 6 (SEQ ID No.:5) | 5'dGGGCCC | GCTGT | ACATG C | ACACG |
| 7 (SEQ ID No.:6) | 5'dGGCC | GACCGC | ACA G C | ACAACCC |
| ROUND 16: Family A | | | | |
| 8 (SEQ ID No.:7) | 5'GGGCCC | GCTGT | ACATG C | ACACG |
| 9 (SEQ.ID No.:7) | 5'GGGCCC | GCTGT | ACATG C | ACACG |
| 10 (SEQ ID No.:7) | 5'GGGCCC | GCTGT | ACATG C | ACACG |
| 11 (SEQ ID No.:7) | 5'GGGCCC | GCTGC | ACGTG C | ACACG |
| 12 (SEQ ID No.:8) | 5'GGGCCC | GCTGT | ACACG C | ACACG |
| ROUND 16: Family B | | | | |
| 13 (SEQ ID No.:9) | 5' CCC | GTTGT | TGTCCCACT | CCACG |
| 14 (SEQ ID No.:10) | 5' CCC | GTTGT | TGTCCCGCT | CCACG |

*Sequences are aligned to highlight the consensus elements (underlined). All sequences are written such that the first six flanking 5' and 3' primer sequences are all 5'GCTTCG and 5'CTCACC, respectively.

The first selection was carried through 7 iterations. Only 3 clones were selected and sequenced (Table-1) at this stage of the selection process. In all 3 early round clones (3:3), a general consensus sequence was found with a stretch of 8–11 A/C's including the sequences: ACAACCC or ACACACC. NF-IL6 is a CCAAT/enhancer-binding protein (C/EBPβ) with specificity for two CCAAC/T boxes. Thus in these early rounds of selection, the thiophosphate substitution at dA did not dramatically altered the affinity for the "CAAC"-like box.

A second independent selection included 10 iterations and yielding the sequences also shown in Table 1 (4 of 4 clones). As shown in Table 1, the two independent selection studies identified a single unique sequence (compare clones #2 and #7). While the ACAACCC sequence once again appeared (#7), another unique new sequence (dGGGCCC GCTGT ACATG C ACACG, SEQ ID No.: 5, clones #4–6) was found for the entire 22-bp randomized segment. The Table has been divided to emphasize homology among 5–6 bp consensus, putative recognition units:

The 10th pool of the second selection was carried through an additional 6 iterations and in the 7 clones sequenced, two major sequence families were obtained (Table 1): Family A) typified by 5'dGGGCCC GCTGT ACATG C ACACG (SEQ ID No.: 7) and Family B) typified by 5'dCCC GTTGT TGTCCCACT CCACG (SEQ ID No.: 9). Within these 22-base sequences only 1 or 2 base changes were found for each family (3 of the 7 were identical sequences; clones #8–10). Note that even by round 10, three members of the 22-base sequence are identical to the A family consensus sequence (clones #4–6). Family B retains the early round CAAC.GTTG consensus while family A has lost all "traditional" C/EBPβ CAAC/T box sequence homology. An additional group of 25 clones were sequenced (data not shown) and the 22-mers were found to also fall within the two families (identical to the consensus sequence or differing by only 1 nucleotide).

These results differ from normal phosphate ester backbone in vitro selection studies with NF-IL6, where a traditional CAAC box was identified using the same TCD of NF-IL6 and 66-mer library under identical selection conditions. Osada, et al. (*J. Biol. Chem.* (1996) 271:3891), used full-length C/EBPβ and a 16 nucleotide randomized library to determine a 10-bp consensus sequence showing the expected two half-site GTTGC.GCAAC in a palindromic sequence as shown in Table 2.

TABLE 2

Comparison of Putative Phosphodiester and
Thiophosphate Consensus Recognition Sequences

| | | |
|---|---|---|
| Consensus phosphate ester (Osaka) | GTTGC GCAAC | (SEQ ID No.: 11) |
| Consensus thiophosphate ester (Family A) | GCTGT ACATG | (SEQ ID No.: 12) |
| Consensus thiophosphate ester (Family B) | GTTGT CCCAC | (SEQ ID No.: 13) |
| | or GTTGT TGTCC* | (SEQ ID No.: 14) |

*(alignment of a consensus sequence is more difficult for Family B members)

Thiophosphate substitution of dA altered the sequence selected, thereby eliminating the sequential AA consensus sequence (Family A only) found in all other phosphate selection studies.

In both normal phosphate and thiophosphate duplex 10-mers, 4–5 dA's may be found, indicating that thiophosphate substitution for the dA residues has not had a deleterious effect on binding.

D. Affinity Measurements by Fluorescence Polarization

The affinity of the selected oligo's or libraries have been measured by fluorescence anisotropy (Heyduk et al. *Proc. Natl. Acad. Sci., U.S.A.* (1990) 87: 1744). Fluorescence polarization titrations using increasing concentrations of the recombinant protein to bind a palindromic 5'-labeled fluorescein C/EBPβ 20-mer binding site with a normal phosphate ester backbone (dTGCAGATTGCGAATCTGCA: SEQ ID NO.: 15) gave an observed binding constant, $K_{obs}$, of 10 nM.

Thiophosphate 66-mers were PCR amplified, phenol extracted and ethanol precipitated. DNA purity was >95% as assessed by PAGE gels. Varying concentrations of 66-mers, 5'-Labeled fluorescein-20-mer palindromic binding site and NF-IL6 TCD dimer were incubated in 10 mM Tris, pH 7.5, 50 mM KCl, 1.0 mM DTT buffer for 1 hour prior to fluorescence polarization measurements. Concentrations of 66-mer were calculated at 20 $OD_{260}$/mg. The observed binding constant, $K_{obs}$, represented the 66-mer concentration providing a 50% decrease in the fluorescence polarization intensity change. Fluorescence polarization titrations were carried out on a Panvera Beacon polarimeter.

The monothiophosphate libraries and individual 66-mer sequences were used as competitors to dissociate a fluoroscein-labeled, normal backbone duplex C/EBPβ 20-mer bound to the bZIP protein. As shown in FIG. 1, an individual monothiophosphate 66-mer cloned from the 10th selection round (clone #7) gave a $K_{obs}$ of <2 nM. DTT and 50 to 400 mM KCl).

Figure 2:
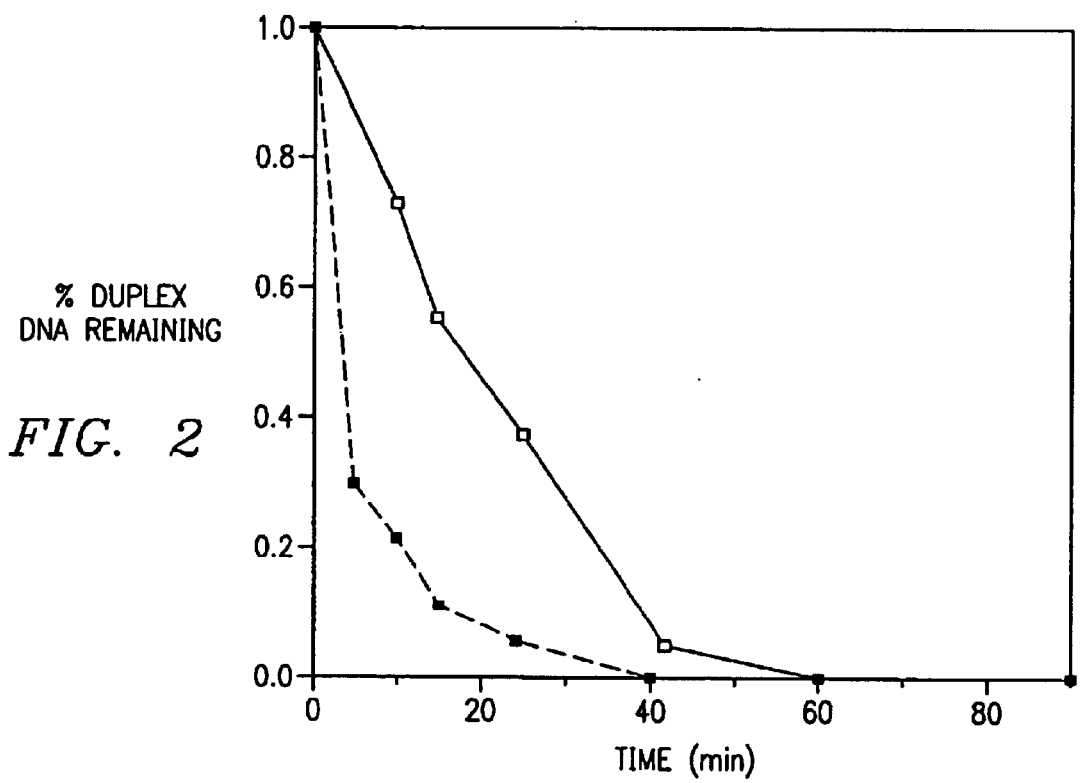
FIG. 2 depicts relative sensitivity of Family A 66-mers to degradation by DNase I. Unmodified, phosphoryl duplex (●) and monothiophosphorylated at non-primer dA sites only (□)

FIG. 2 depicts relative sensitivity of Family A 66-mers to degradation by DNase I. Unmodified, phosphoryl duplex (●) and monothiophosphorylated at non-primer dA sites only (□).

Figure 3A:
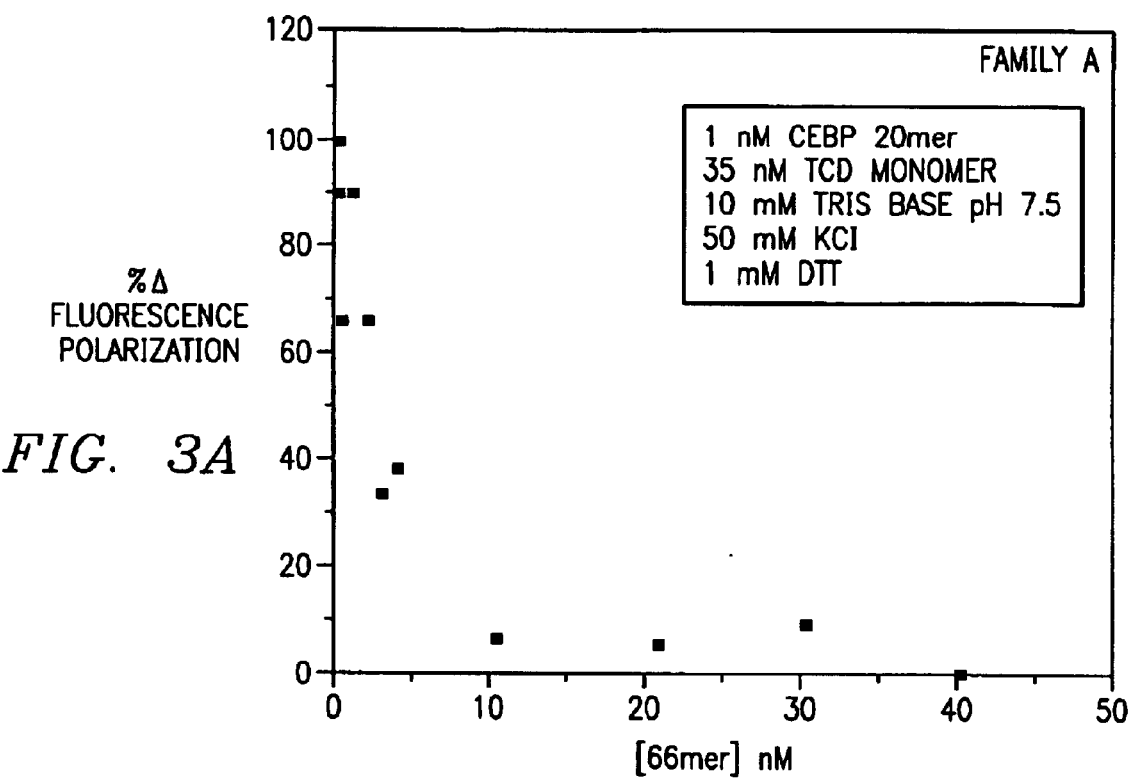
FIG. 3 is a negative control, at a concentration of up to 4 μm, thiophosphate clone 98 (Family A) was shown not to bind to another transcription factor, NF-κB (p65 dimer)
Figure 3B:
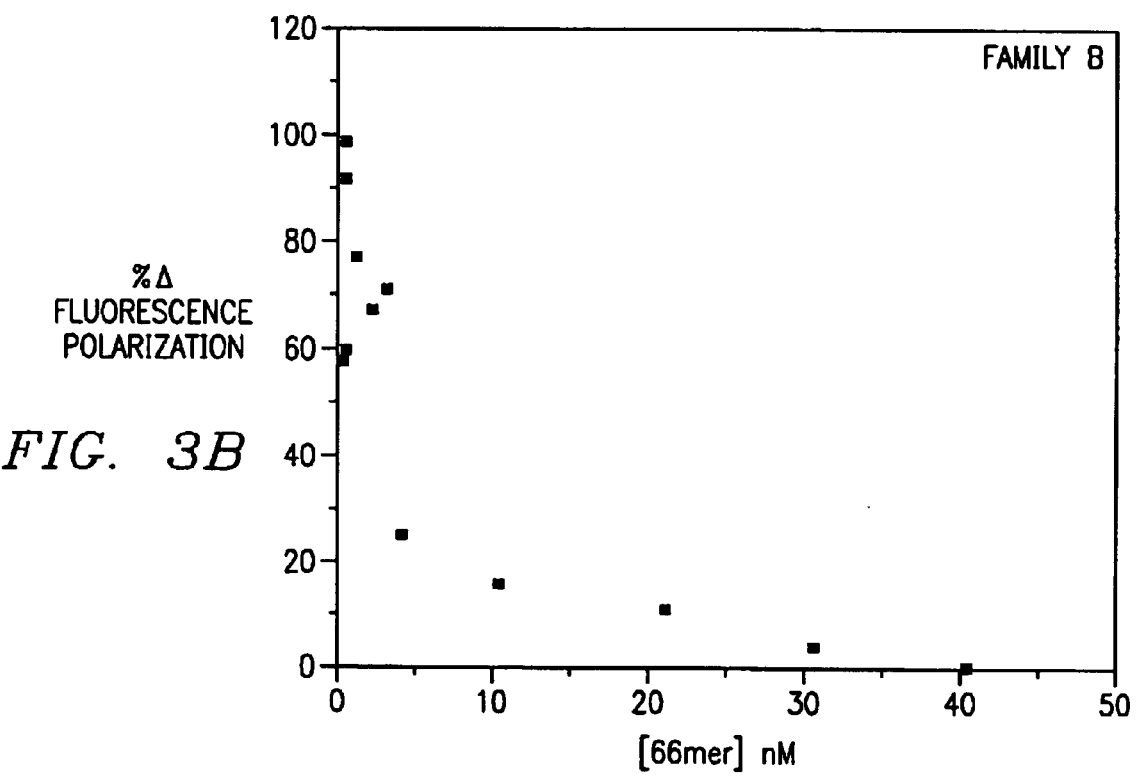

Following a similar competitive titration, monothiophosphate (at dA) clones #8 and 13 (consensus Family A and B, respectively) also gave a Kb of <2 nM (FIG. 3). As a negative control (data not shown), at a concentration of up to 4 μM, thiophosphate clone #8 (Family A) was shown not to bind to another transcription factor, NF-κB (p65 dimer).

Figure 4A:
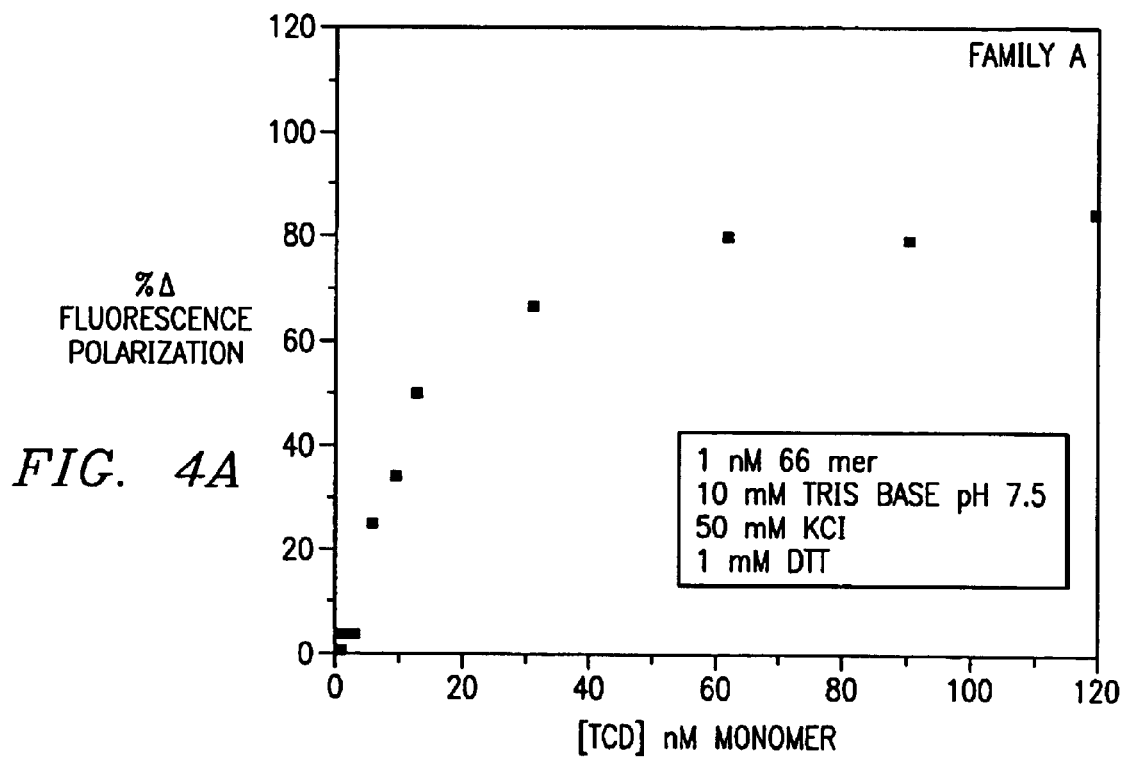
FIG. 4 depicts these titrations performed directly whereby each aptamer was fluorescein labeled and the protein was titrated into the solution.
Figure 4B:
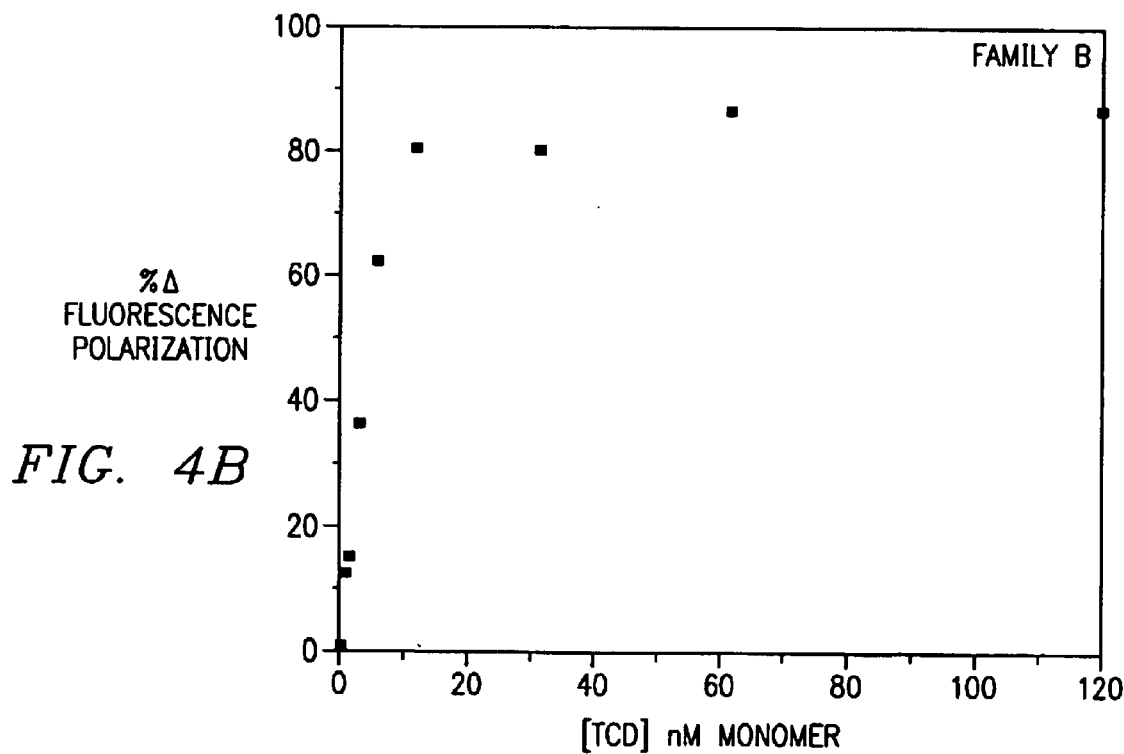

These titrations were also performed directly where each aptamer was fluorescein labeled and the protein was titrated into the solution. These assays gave similar estimates of the binding constants (Family A 5 nM and Family B 3 nM, monomer concentration giving 50% saturation, FIG. 4).

Stoichiometric titration of 66-mers with TCD established that later rounds (FIG. 1) bound the protein dimer with an approximate 2:1 (protein dimer: DNA duplex) stoichiometry. Initial rounds bound to TCD with a 1:1 stoichiometry (FIG. 1). This change in stoichiometry may explain the remarkable selection of a full 22-base sequence when the NF-IL6 consensus site is believed to be only 10 bases in length.

The crystal structure of leucine zipper proteins such as GCN4 and AP-1 in the DNA cocrystal are coiled coils (Ellenberger, et al., *Cell* (1992) 71: 1223), with the basic region coiling into a helix to bind in the major groove in each of the half sites. In a bZIP protein such as NF-IL6, it would be expected that each basic region of the protein binds as an alpha-helix to the two CAAC/T half-sites in the generally palindromic recognition sequences.

In order to explain the 2:1 stoichiometry for binding Family A consensus 22-mer sequence, two TCD dimers must be capable of orienting on the duplex. Note that the Family A 22-mer contains the consensus sequence:

5' dGGGCC C GCTGT ACATG C ACACG     (SEQ ID No.: 7)

CCCGG G CGACA TGTAC G TGTGCd 5'     (SEQ ID No.: 16).

There are three very similar sequences shown above in bold: 5'ACAGC, 5' ACATG, 5'ACACG, which were being selected even in rounds 7–10, and remarkably, in the same orientation and order shown above (Table 1). This degree of conservation suggests that one TCD dimer can bind with each basic recognition helix interacting with each of the 5 nucleotide sequences (containing ACA.TGT triplets) shown in bold. The second TCD dimer may bind to one of the two basic recognition helices recognizing the 3rd 5 nucleotide sequence in bold.

The six N-terminal residues of TCD are required for binding to the NF-IL6 consensus sequence (Brasier et al. *J. Biol. Chem.* (1994) 269: 1034). Although not part of the basic domain of the protein, the NMR structural studies conducted by the present inventors demonstrated that there is considerable helical content in this region.

E. Nuclease Resistance of Thiolated Aptamers

The sensitivity of the duplexes to DNase I degradation was monitored by native PAGE. Reaction mixtures contained either 40.5 or 33.8 μg/ml duplex (phosphoryl or thiophosphoryl, respectively) in 205 μL of 50 mM Tris, 10 mM $MgCl_2$, 50 μg/mL BSA, pH 7.5 buffer and 0.12 pg/mL DNase I (Sigma). Aliquots (20 μl) were removed at specific time points and the hydrolysis quenched by adding 4 μl 0.5 M EDTA, 20 μl 90% formamide, followed by boiling and storing at 0° C. Gels were scanned and the 66-mer lane integrated using an Image ID gel scanner (Pharmacia).

As shown in FIG. 2, thiophosphorylation of the Family A 66-mer at only the dA sites (excepting the primers) results in a duplex that is more resistant to DNase I degradation than the unmodified 66-mer. Increased nucelase resistance was found for both endonucleases such as DNase I or exonucleases such as Bal 31.

EXAMPLE 2

Specificity of NF-κB Monothioate Aptamers

A. Aptamers p oligonucleotide duplex of the sequence 5'-CCAG GAGA TTCC AC CCAG GAGA TTCC AC CCAG GAGA TTCCAC-3', termed CK-1 (SEQ ID NO.: 16), was identified by Sharma, et al. (*Anticancer Res.* (1996) 16:61), to be an efficient NF-κB binding aptamer. The original phosphodiester CK-1 duplex sequence contains 3 tandem repeats of a 14-mer NF-κB binding sequence (5'-CCA GGA GAT TCC AC 3',a.k.a., CK-14 and having SEQ ID NO.: 17). The CK-1 42-mer duplex oligonucleotide is said to represent the NF-κB binding site in the G-CSF and GM-CSF promoter to which RelA but not the p50 homodimer binds. The CK-1 decoy ODN has been shown to decrease the expression of cytokine and immunoglobulin genes in cultured mouse splenocytes. (Khaled, et al., *Clinical Immunology & Immunopathology* (1998) 86:170). It was argued that CK-1 specifically targeted the activators of NF-κB regulated gene expression, p50/c-Rel or RelA dimers, and not the repressive p50 homodimers.

It is unlikely, however, that unmodified or phosphodiester ODNs may be useful as therapeutics because of their short half-life in cells and serum. Phosphorothioate and dithioate internucleotide linkages are therefore needed. Presumably for this reason Sharma, et al. (*Anticancer Res.* (1996) 16:61), also reported inhibition of NF-κB in cell culture using fully thiolated [S]-ODN duplex decoys with the NF-κB binding consensus-like sequence (GGGGACTTCC SEQ ID NO.: NO.: 18).

To determine the effect of monothiolation of the CK-14 sequence on NF-κB binding, the present inventors chemically synthesized a monothiolated CK-14 sequence by sulfur oxidation with phosphoramidite chemistry, the same method used by Sharma to generate the [S]-(GGGGACTTCC) duplex. Using this method, the monothiolated ODN contain in principle $2^{82}$ or $10^{24}$ different stereoisomers.

B. Binding of Monothiolated ODN to Various NF-κB/Rel Dimers

The present applicants used recombinant protein homodimers of p50, p65, and c-Rel showing that the phosphodiester CK-1 sequence could bind to and compete for binding to p65 homodimer, but not p50/p50, in standard electrophoretic mobility shift assays (EMSA), confirming the published results. (Sharma, et al., *Anticancer Res.* (1996) 16: 61).

CK-1 did bind and compete for binding to c-Rel. Oligonucleotides containing only one copy of the binding site in either a 14-mer (5'-CCA GGA GAT TCC AC; CK-14) or a 22-mer duplex ODN (an IgKB site) behaved similarly to the longer version, and served as the first target for the synthesis of various hybrid backbone-modified aptamers.

Figure 5A:
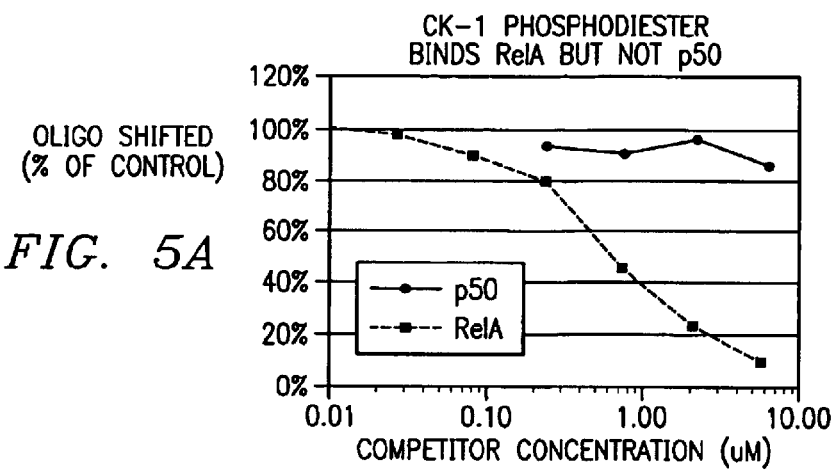
FIG. 5 shows results of a competition assay for binding CK-1 42-mer aptamers.
Figure 5B:
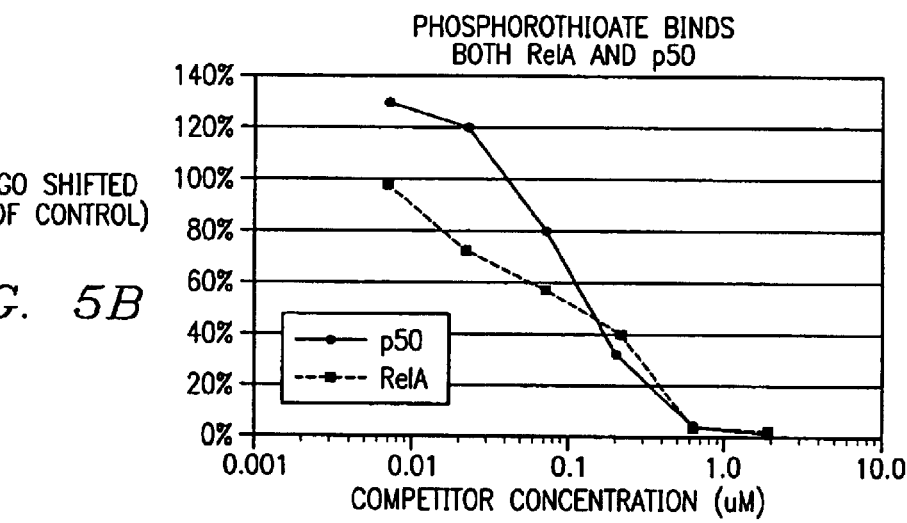

FIG. 5 is a graph showing the binding of duplex ODNs using Sharma's teachings and demonstrating that the phosphodiester of CK-1 binds only p65/p65 [FIG. 5 (A)] and not p50 homodimer. In standard competitive binding assays, $^{32}$P-IgκB promoter element ODN duplex was incubated with recombinant p50 or p65 and competitor oligonucleotide (A) phosphodiester CK-1; (B) phosphorothioate CK-1. The reactions were then run on a nondenaturing polyacrylamide gel, and the amount of radioactivity bound to protein and shifted in the gel was quantitated by direct counting. When fully thiosubstituted, the phosphorothioate CK-1 aptamer [FIG. 5(B)] equally inhibited p65/p65 and p50/p50. It is the recognition that [S]-ODNs with large numbers of phosphorothioate linkages are "sticky" and tend to bind with poor specificity to proteins that led to one of the embodiments of the present invention. Using the method disclosed herein it was determined that if the number of phosphorothioate linkages is reduced to only 2–4, specificity can be restored, but binding is not enhanced. The original published results of Sharma describe only the specificity of the phosphodiester oligonucleotides and do not address the problem of altered specificity of the phosphorothioates.

EXAMPLE 3

Thioselection of Phosphorodithioate Aptamers Binding to NP-κB

A. Library Generation

A random combinatorial library of normal phosphoryl backbone oligonucleotides was synthesized by an automated DNA synthesizer that was programmed to include all 4 monomer bases of the oligonucleotide during the coupling of residues in a randomized segment. A 62-mer has been constructed with a 22 base pair random central segment flanked by 19 and 21 base pair PCR primer regions: 5'dATGCTTCCACGAGCCTTTC($N_{22}$)CTGCGAGGCGGTAGTCTATTC3' (SEQ ID NO.: 19). The resulting library thus exists as a population with potentially $4^{22}$ ($10^{13}$) different possible sequences.

B. Thiophosphate Substitution and Selection

The duplex oligonucleotide library with phosphoromonothioate backbone substituted at dA positions was then synthesized by PCR amplification of the 62-mer template using commercially available Taq polymerase and using a mix of dATP(αS), dTTP, dGTP and dCTP as substrates. As will be appreciated by those of skill in the art any of the nucleotides may be the one or more nucleotides that is selected to have the thiol modification.

The random library generated thereby was screened to identify sequences that have affinity to the p65 homodimer. PCR amplification of the single stranded library provides chiral duplex phosphorothioate 62-mer at all dA positions other than the primers. This material was then incubated with the p65 dimer for 10 minutes at 25° C. and filtered through pre-soaked Millipore HAWP25 mm nitrocellulose filters. The combinatorial thiophosphate duplex library was successfully screened for binding to the p65 dimer. The filter binding method was modified to minimize non-specific binding of the thiophosphate oligonucleotides to the nitrocellulose filter.

The thiophosphate substituted DNA was be eluted from the filter under high salt and under protein denaturing conditions. Subsequent ethanol precipitation and another PCR thiophosphate amplification provide product pools for additional rounds of selection. In order to increase the stringency of binding of the remaining pool of DNA in the library and select tighter binding members of the library, the KCl concentration was increased in subsequent rounds from 50 to 200 mM. The stringency of selection was also manipulated by increasing the volume of washing solution as the number of iterations are increased. A negative control without protein was performed simultaneously to monitor any non-specific binding of the thiophosphate DNA library to the nitrocellulose filter.

Thioselection against the p65.p65 of NF-κB was carried through 10 rounds. Cloning and sequencing according to standard methods known to those in the art was performed after 10 iterations had been completed. From these rounds of selection eight (8) sequences, shown here as the duplex sequence, were obtained:

1) 5'GGG GCG GGG GGA TAT GGA CAC C3'   (SEQ ID
   3'CCC CTC CCC CCT ATA CCT GTG G5'    NO.: 20)

2) 5'GGG CTG GTG TGG TAG ACT CCC C3'   (SEQ ID
   3'CCC GAC CAC ACC ATC TGA GGG G5'    NO.: 21)

3) 5'CCC GCC CAC ACA CAC CGC CCC C3'   (SEQ ID
   3'GGG CGG CTG TGT GTG GCG GGG G5'    NO.: 22)

-continued

```
4) 5'GGG CCG GGA GAG AAC ATA GCG AC3'     (SEQ ID
   3'CCC GGC CCT CTC TTG TAT CGC TG5'     NO.: 23)

5) 5'CCC NCN NNC ACA CAC CGC CCC C3'      (SEQ ID
   3'GGG NGN NNG TGT GTG GCG GGG G5'      NO.: 24)

6) 5'GGT ATA CTC TCC GCC CCT CCC C3'      (SEQ ID
   3'CCA TAT GAG AGG CGG GGA GGG G5'      NO.: 25)

7) 5'CCC ACA TGT ACA CGC CGC CCC CGC CC3' (SEQ ID
   3'GGG TGT ACA TGT GCG GCG GGG GCG GG5' NO.: 26)

8) 5'CCC ACA TGN ACA CNC CGC CCC C3'      (SEQ ID
   3'GGG TGT ACN TGT GNG GCG GGG G5'      NO.: 27)
```

The sequences were lined up by either their 5'-3' or 3'-5' ends choosing the G rich strand, thus finding a consensus pattern in the sequences. The sequence obtained for a 22-nucleotide variable region in which all dAs were thiolated, which shows somewhat of a conserved consensus site containing two tandem decameric KB motifs separated by G*. A general consensus site for the 22-nt variable region of a new combinatorial library was identified which binds tightly to NF-κB:

GGGCG T ATAT G* TGTG GCGGG GG (SEQ ID NO.: 28). Surprisingly, this sequence differs from the CK-1 sequence of 14 bases. The GGGCG is conserved at both ends of the sequence and finishes with a purine pyrimidine alternation of bases (ATAT or GTGT) centered around the G*. The binding characterisitcs of this 22-mer suggests that two p65 homodimers bind to the selected sequence and that the p65 homodimers interact in a head to head fashion enhancing their affinity to the mutated DNA.

A binding study done with the sequences from round 10 by $^{32}$P labeling EMSA showed specific binding of the thiolated DNA to the p65 homodimer protein. Thus, as with the NF-IL6 thioaptamer, the present thiophosphate combinatorial selection technology achieved selection of a tight binding aptamer with a sequence that differs from the normal phosphate backbone aptamer selected sequence. Furthermore, the NF-κB thioaptamer exhibits an approximate two-fold, head-to-head symmetry (assuming A, G=Pu in the central 9 bps) centered around G* in the combinatorially selected sequence. This is similar to the NF-IL6 thioselection aptamer, described hereinabove, in which high selection constancy was obtained throughout the full 22-nucleotide variable region, and the stoichiometry indicated that two NF-IL6 bZIP dimers bound per aptamer.

As it appears that two NF-κB dimers bind to the thioselected [S]-ODN, this creates a novel invention providing for the development of even more highly selective thiolated aptamers targeted to specific NF-κB/Rel homo- and heterodimers, based not only on the protein-DNA contacts, but also on protein-protein contacts. Orientation of each of the NF-κB/Rel dimers on such an aptamer will tightly constrain the optimal dimer-dimer contacts and will presumably will differ for each homo- or hetero-dimer. The present invention provides a thioselection methodology that targets any number of different protein-protein complexes, not just those from NF-IL6 and NF-κB/Rel.

Single stranded phosphorothioate selection may be performed in exactly the same manner as the duplex version. The difference will be the method of PCR performed during each iteration. Briefly, one primer in the set of 2 must be 5' biotinylated. Following PCR, the duplex is denatured and the 2 strands separated using an avidin affinity column. In this way, only one strand of the library will be sampled and enriched during each iteration.

EXAMPLE 4

NF-κB Aptamers with Specific Placement of Phosphorodithioates: Synthesis, Purification and Binding to NF-κB One embodiment of the present invention provides a method of preparation of oligonucleotides containing selected phosphorodithioate linkages free of phosphoromonothioate impurities. One such preparation involves solid phase synthesis using the nucleoside phosphorothioamide method followed by PCR to generate achiral phorphorothioate oligonucleotides based on a selected sequence. Oligonucleotides essentially free from detectable phosphomonothioate linkages are provided using ion exchange chromatography, e.g., using a Mono Q ion exchange purification column.

Using this method, aptamers targeting NF-κB that contain thymidine 3'-O-phosphorodithioates in selected positions of an oligonucleotide duplex were synthesized. The total number of dithiolated phosphates was optimized in order to minimize non-specific protein binding while enhancing specific binding to the protein of interest. Binding affinities to NF-κB varied with the number and positions of the dithioate backbone substitutions. An aptamer showing specific binding to a single NF-κB dimer in cell culture extracts was obtained.

In one embodiment, dithiolated [$S_2$]-ODNs were generated using an improved method of solid phase synthesis based on nucleoside phosphorodithioamidite chemistry. Solid-phase synthesis of aptamers containing thymidine 3'-O-phosphorodithioates free of phosphoromonothioates was obtained as follows.

The 14-mer NF-κB binding sequence (5'-CCA GGA GAT TCC AC 3' SEQ ID NO.: 17) was used as the starting point for design of novel NF-κB specific thioaptamers. As it was determined by the present inventors that complete thioation of the CK-1 or CK-14 aptamer results in loss of specificity, it is clear that complete thiolation does not provide an effective agent capable of specifically binding various NF-κB/Rel dimers.

Based on the observation that excess thioation leads to a loss of specificity in the interaction between the thiolated phosphates and the protein, the present inventors selected specific nucelotides thiosubstitution and synthesized 14-mer duplexes with strategically placed dithioate linkages. These substitutions resulted in very significant and surprising effects on the function of the 14-mer sequence. They not only have the extreme "stickiness" of the fully thiolated aptamer but also exhibit altered binding specificity. The present inventors further found that when only one or two phosphodithioate linkages are placed in a molecule, the inhibition/binding of the oligonucleotide to recombinant protein is similar to that of the unsubstituted aptamer.

Figure 6:
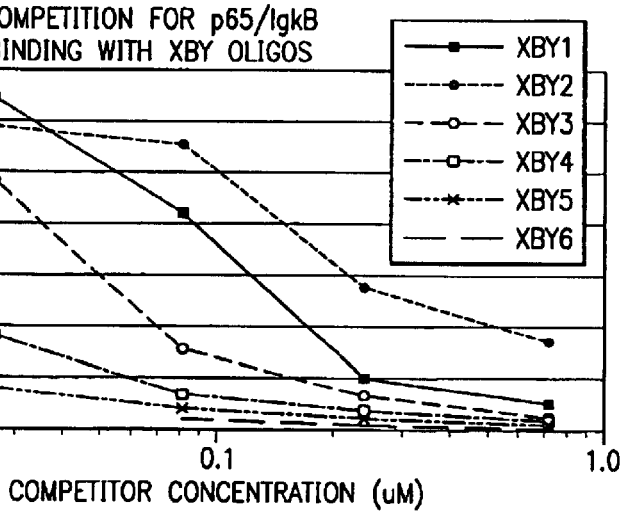
FIG. 6 is a graph showing the inhibition of p65 homodimer binding by [$S_2$]-ODN (XBYs)

FIG. 6 is a graph showing the competitive binding of the six XBY oligos. With more substitutions, binding by the oligonucleotide increases dramatically. In standard competitive binding assays, $^{32}$P-IgκB promoter element ODN was incubated with recombinant p65 and varying amounts of XBY decoy competitor. The relative binding ability of the unlabeled ODNs was determined by the concentration needed to effectively compete with the standard labeled ODN. XBY 1 through 6 correspond to CK-14 aptamers with 1 though 6 dithiophosphate substitutions, respectively.

A. Synthesis of Thymidine 3'-O-phosphorodithioates

The thymidine 3'-O-phosphodiesters of Scheme 1:1 and its complementary sequence of 5'-GTGG AATC TCCTGG- 3' (SEQ ID NO.: 29) were replaced with thymidine 3'-O-phosphorodithioates in two or four positions. The nucleoside phosphorothioamidite approach was used to synthesize the [S$_2$]ODNS according to the method of Wiesler, et al., *J. Org. Chem.* (1996) 61:4272. Using this method, thymidine S-(β-thiobenzoylethyl)pyrrolidinophosphorothioamidite was prepared in ca. 80% yield. The purity (ca. 80%) was assayed via $^{31}$P NMR ($\delta^{31}$ p 161.1, 164.7 CD$_2$Cl$_2$). In initial determinations, oligonucleotide Scheme 1:A(2) (SEQ ID NO.: 40) containing two thymidine 3'-O-phosphorodithioate linkages was first prepared on a Gene Assembler Plus (Pharmacia) (1.3 μmole).

A modification of the normal coupling cycle for the phosphorothioamidite DMT yielded a coupling efficiency of ca. 98–99%. Briefly, sulfurization was carried out with $^3$H-1,2-benzodithiole-3-one, 1,1-dioxide (Beaucage Reagent), resulting in a normal phosphoramidite DMT-efficiency of ca. 99%. The crude oligonucleoside phosphorodithioate (DMT on) was cleaved from the support and deblocked by treatment with 28–30% aqueous ammonia (ca. 1.5 ml) in a tightly stoppered vial at 55° C. for 16 hours. After removal of the support, the ammonia solution was concentrated and subjected to $^{31}$P NMR analysis, which showed the correct ratio of phosphorodithioate linkages ($\delta^{31}$P ca. 113 ppm) to phosphate linkages ($\delta^{31}$ P ca. 0 ppm). $^{31}$P NMR analysis of this oligonucleotide, however, also showed some small amounts of nucleoside phosphoromonothioates ($\delta^{31}$ P ca. 58 ppm) as a previously noted contaminate of the procedure. (Okruszek, et al., *J. Org. Chem.* (1995) 60:6998; Wiesler, et al., *J. Org. Chem.* (1996) 61:4272.)

The 5' O-DMT-oligonucleotide Scheme 1:A(2) (SEQ ID NO.: 30) was purified by reverse-phase HPLC (Hamilton PRP-1 column), desired fractions were collected and evaporated. Detritylation was accomplished with 75% acetic acid for 15 min at 0° C. After three diethyl ether extractions, the solution was neutralized with aqueous ammonia, followed by lyophilization. $^{31}$P NMR showed increased amounts of phosphoromonothioates, suggesting that the deprotection step leads to some desulfurization. If the final 5'-O-DMT protecting group was removed on the synthesizer while still on the solid support, however, desulfurization was diminished.

B. Purification of Thymidine 3'-O-phosphorodithioates

The crude oligonucleotides were dissolved in about 1.0 ml of water, and purified by FPLC ion exchange (Pharmacia Mono Q 5/5) chromatography using the following gradient for purification/time: 0–80 min, 0–100 B %; 80–85 min, 100 B %; 85–89 min, 100–0 B % and the following mobile phase solvents: A) 25 mM Tris-HCl, 1 mM EDTA, pH 8; and B) 25 mM Tris-HCl, 1 mM EDTA, 1.0 M NaCl, pH 8. $^{31}$P NMR showed that the oligonucleotide phosphoromonothioate impurities were not present indicating that Mono Q ion exchange column chromatography is able to remove these impurities.

C. Generation of Preferred Substituted Oligonucleotides

The above methodology was applied to the design and preparation of complementary sequences containing two or four thymidine 3'-O-phosphorodithioate linkages. The purity of each oligomer (Scheme 1:A(3–5): SEQ ID NO.: 31–33) was assayed by $^{31}$P NMR.

Figure 8:
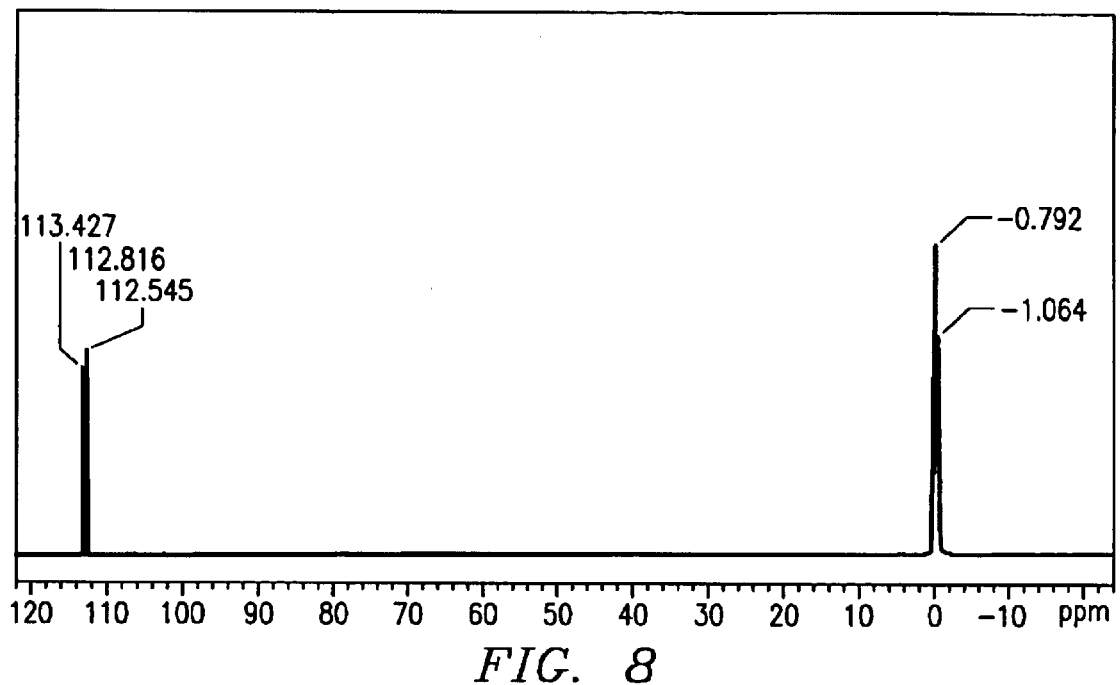
FIG. 8 shows $^{31}P$ NMR spectrum of thymidine 3'-O-phosphorodithioate single stranded sequence 5 (SEQ ID NO.: 43) recorded on a Varian Unity plus spectrometer operating at 242 MHZ.

FIG. 8 shows a representative $^{31}$P NMR spectrum of an oligonucleotide Scheme 1:A(5) (SEQ ID NO.: 33) containing four 3'-O-phosphorodithioate linkages showing the absence of any phosphoromonothioate linkages. The $^{31}$P NMR spectrum of 5 was recorded on a Varian Unity plus spectrometer operating at 242 MHz. The sample contained ca. 40 OD A$_{260}$ units dissolved in 500 μl of D$_2$O. Chemical shifts were referenced to 85% phosphoric acid. The molecular structure of oligonucleotide 5 was further confirmed by MALDI-MS, the calculated molecular weight is 4422.92 and the molecular weight observed was 4426.13. Peaks corresponding to M-16 or M-32 were not observed confirming the absence of significant quantities of oligomers with phosphoromonothioate linkages.

Scheme 1. A: Single Strands:

Single-stranded oligonucleotides 1–5 synthesized are shown, in which thymidine 3'-O-phosphorodithioate was incorporated in two or four positions.

| | | |
|---|---|---|
| 5'-CCAGGAGATTCCAC-3' SEQ ID NO.: 17 | | 1. |
| 5'-CCAGGAGAT$_{S2}$T$_{S2}$CCAC-3' SEQ ID NO.: 30 | | 2. |
| 5'-GT$_{S2}$GGAATCTCCT$_{S2}$GG-3' SEQ ID NO.: 31 | | 3. |
| 5'-GTGGAAT$_{S2}$CT$_{S2}$CCTGG-3' SEQ ID NO.: 32 | | 4. |
| 5'-GT$_{S2}$GGAAT$_{S2}$CT$_{S2}$CCT$_{S2}$GG-3' SEQ ID NO.: 33 | | 5. |

Scheme 1. B. Duplexes:

Duplex aptamers were annealed at 15.75 μM of each strand in 10 mM Tris-HCl pH 7.5, 2 mm MgCl$_2$, 50 mM NaCl, 1 mM EDTA.

```
 6. 5'-CCAG GAGATTCCAC-3'                SEQ ID NO.: 34
    3'-GG_S2 TCCTCTAAGG_S2 TG-5'

7. 5'-CCAGGAGATTCCAC-3'                 SEQ ID NO.: 35
    3'-GGTCC_S2 TC_S2 TAAGGTG-5'

8. 5'-CCAGGAGATTCCAC-3'                 SEQ ID NO.: 36
    3'-GG_S2 TCC_S2 TC_S2 TAAGG_S2 TG-5'

9. 5'-CCAGGAGAT_S2 T_S2 CCAC-3          SEQ ID NO.: 37
    3'-GG_S2 TCCTCTAAGG_S2 TG-5'

10. 5'-CCAGGAGAT_S2 T_S2 CCAC-3'         SEQ ID NO.: 38
    3'-GGTCC_S2 TC_S2 TAAGGTG-5'

11. 5'-CCAGGAGAT_S2 T_S2 CCAC-3'         SEQ ID NO.: 39
    3'-GG_S2 TCC_S2 TC_S2 TAAGG_S2 TG-5'
```

D. Binding Specificity of the Thiolated Aptamers

Figure 9:
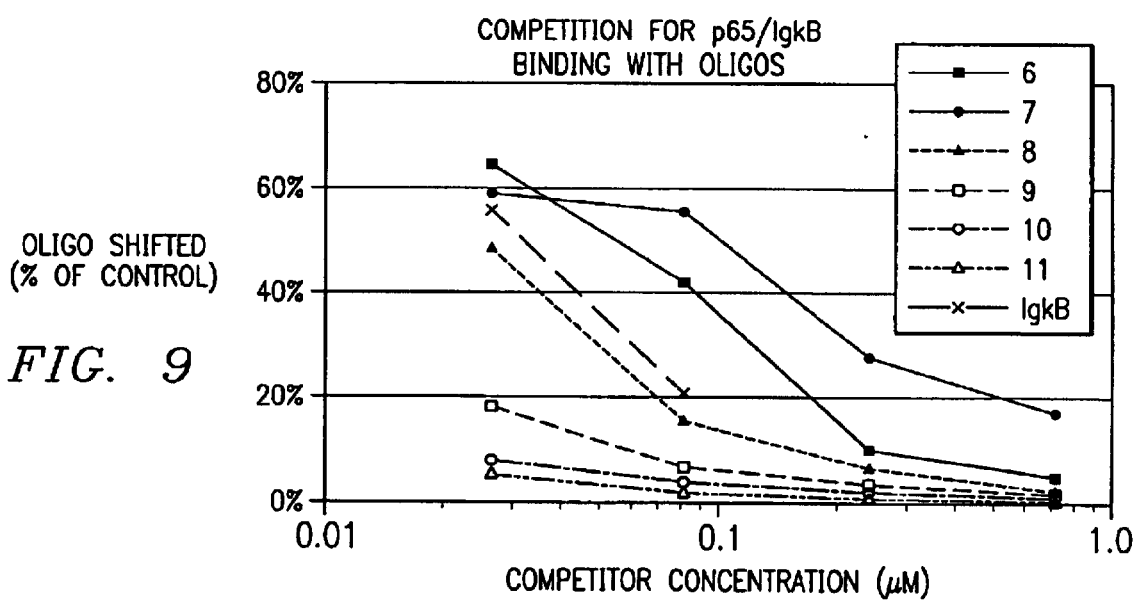
FIG. 9 shows inhibition of p65 homodimer binding by thymidine 3'-O-phosphorodithioate duplex aptamers 6–11 (SEQ ID NOS.: 34–39)
Figure 10A:
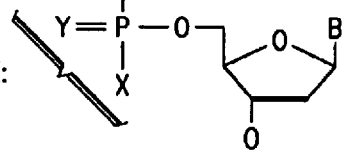
FIG. 10a shows a diagrammatic representation of the sites of thiophosphate and dithiophosphate modification of the nucleotide backbone.
Figure 10B:
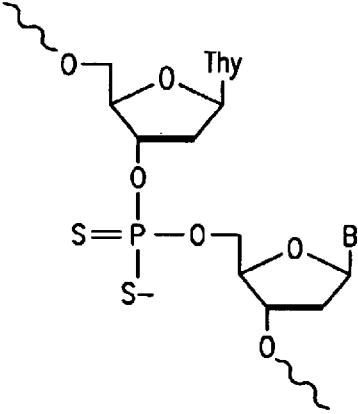
FIG. 10b shows a diagrammatic representation of thymidine 3'-O-phoshorodithiophosphate.

In an alternate embodiment, duplex [S$_2$]-ODN aptamers Scheme 1:B(6–11) (SEQ ID NO.: 34–39) were prepared and their binding to NF-κB was analyzed. In standard competitive binding assays as shown in FIG. 9, $^{31}$P end-labeled IgκB promoter element oligonucleotide (5'-AGTT GAGG GGAC TTTC CCAG GC-3'; SEQ ID NO.: 40) was incubated with recombinant p65$^{28}$ and varying amounts of competitor aptamers Scheme 1:B(6–11). The relative binding affinity of the unlabeled aptamers was determined by the concentration needed to effectively compete with the standard labeled aptamer. When only one strand of the aptamers contain thymidine 3'-O-phosphorodithioate Scheme 1:B(6–8), the inhibition/binding of the aptamer to protein was similar to that of the unsubstituted aptamer. With increased dithioate substitution on both strands, binding by the [S$_2$]-ODNs increased dramatically. FIG. 9 shows the inhibition of p65 homodimer binding by dithioate substituted aptamers Scheme 1:B(6–11).

One aptamer of the present invention, duplex aptamer Scheme 1:B(11), SEQ ID NO.:39 (also termed XBY-6 herein), contains six dithioate linkages on the two strands. It was found that unlike the fully monothio-substituted aptamer [S]-ODN CK-14, the present dithiolated [S$_2$] hybrid backbone ODN XBY-6 binds more tightly to recombinant p65/p65 (5 to 15 fold) than to the recombinant p50 homodimer in vitro. Significantly, the XBY-6 aptamer also binds to a single NF-κB dimer in cell extracts, while the standard unmodified phosphodiester ODN showed no NF-κB -specific binding in extracts.

The following studies demonstrate the NF-KB subunit specificity of aptamer binding. Thymidine 3'-O-phosphorodithioate duplex aptamer Scheme 1:B(11) (SEQ ID NO.: 39) was incubated with radiolabeled oligonucleotide with 7OZ/3 cell nuclear extract in the presence or absence of anti-p50 antibody. Protein bound ODN duplex was separated on a non-denaturing gel.

It was found that XBY-6 shifts only one complex in nuclear extracts from 70Z/3 cells. By using specific antibodies to supershift the complex, p50 was identified as one component of the complex. Since XBY-6 binds more poorly to p50/p50 (by a factor of 5–15-fold) than p50/p65, the shifted band is unlikely to represent the p50 homodimer. Although this band does not co-migrate with either the p50/p50 or p50/p65 bands, the altered chemical structure changes the mobility of the ODN. Only one major band was seen, however, even though the lysate contains at least two major distinguishable NF-κB complexes (p50 homodimers and p50/p65 heterodimers) (data not shown). By binding to p50 but not p65, it is clear that the thioselected aptamer of the present invention can distinguish among various NF-κB dimers within the cell.

EXAMPLE 5

Split Synthesis Combinatorial Chemistry
A. Library Generation

A split synthesis combinatorial chemistry method was developed to create a combinatorial library of [$S_2$]-ODN agents. In this procedure each unique member of the combinatorial library is attached to a separate support bead. Proteins that bind tightly to only a few of the $10^4$–$10^6$ different support beads can be selected by deprotecting a single aptamer bead in a 96-well plate in a high-throughput assay, or by binding the protein directly to the beads and then identifying which beads have bound protein by immunostaining techniques.

To introduce many copies of a single, chemically pure [$S_2$]-ODN onto each bead, a "mix and separate" method was used. Applying this method to NF-κB, the XBY-6 sequence was synthesized as a single-strand 33-mer hairpin containing a TTTT loop as follows:

5'dCCAGGAGAT*TCCACTT-TTGT*GGAATC TCC
TGGA (SEQ ID NO.: 40)

T* is randomized as either a phosphorodithioate or a normal phosphate ester.

This was achieved by modifying the normal solid-phase synthesis of the 33-mer. On a two column DNA synthesizer, a different thiophosphoramidite was first added onto both identical supports (at the appropriate sequence position) on each column. After the normal cycle of S oxidation and blocking (which introduces the dithiophosphate linkage at this position), the support beads were removed from the columns, mixed together and the mixture reintroduced into both columns. At the next randomized position (the second T in the above sequence), a thiophosphoramidite with either a different or the same base (T in the example cited) was then added to each of the columns. Cycles of mixing and separating may be continued for n internucleoside dithiophosphates (n=2 in the present example). The dithiophosphate-modified oligonucleotide was deblocked and either removed from the column (and purified) or retained on the column.

B. NF-κB Selection

Target protein is bound to the beads and washed at various salt and urea concentrations to remove weakly bound proteins. Support beads that bind the protein may be visualized under a microscope by adding an immunostaining agent targeted to the protein, and physically separated from the unstained (unbound) beads. Alternatively, multiwavelength flow cytometry and cell sorting can be used for visualization and sorting of the protein-bound aptamer beads. As another alternative, high-throughput screening of the purified aptamers (one from each bead) can be used in n-well selection plates.

C. Sequencing

After selection, the site of dithiophosphate modification may be identified for the separated aptamer (or covalently linked aptamer released from the bead). The difference in chemical reactivity between phosphate and phosphorothioate and dithioates is exploited to directly sequence the aptamer and locate the thiolated internucleoside linkages independent of the base sequence. Briefly, after $^{32}$P-end labeling, the hybrid [$S_2$]-ODNs are alkylated with agents such as 2-iodoethanol, while normal phosphates are not. Addition of dilute NaOH cleaves only at the thio- (or dithio-) phosphate. Standard sequencing gel electrophoretic methods are used to determine the size of the cleaved fragments, and thus the position of the modified phosphate backbone (Gish, G. & Eckstein, F., *Science* (1988)240:1520).

When sequencing of the dithioates was conducted using this technique, reaction of O,O-diethyldithiophosphate with iodoethanol gave quantitatively dithiophosphate triester, which was stable under the condition of alkylation. With the addition of dilute sodium hydroxide, the triester was hydrolyzed to O,O-diethyl phosphate. When the d[$T_{S2}$T] was treated with 2-iodoethanol, however, direct conversion to TpT, thymidine 5'-O-monophosphate and thymidine 3'-O-monophosphate were assayed by $^{31}$P NMR. TpT was identical to the authentic sample by comparing their retention time on RP-HPLC chromatography. The difference in reactivity between $T_{PS2}$T and 11-mer oligonucleotide containing a single monothioate linkage was observed.

D. Separation by Anion-exchange Chromatography on a Mono Q Column

A variety of separation strategies have been used for the analysis and purification of synthetic phosphorodithioate oligonucleotides. The selection of the appropriate separation method is dictated primarily by the oligonucleotide purity requirements of the application. Since chemical by-products generated in the synthesis of phosphorodithioates may be toxic to cells in tissue culture or in vivo, the chemical authenticity of a particular oligonucleotide phosphorodithioate may be crucial if the oligonucleotide is to be administered in humans as a drug. The ability to purify oligonucleotide phosphorodithioates on a routine basis is essential.

Purification of oligonucleotide phosphorodithioates bearing less than 50% dithioate linkages by ion-exchange HPLC has been mentioned. Neither the separation of synthetic phosphorodithioate oligonucleotides from phosphoromonothioate impurities by anion-exchange chromatography nor dithio-dependent separation has been previously achieved.

Therefore, provided herein is a new and effective method of ion-exchange FPLC separation of synthetic phosphorodithioate oligonucleotides from phosphoromonothioate contaminants by anion-exchange chromatography on a Mono Q column.

Oligodeoxyribonucleotides of the base sequence 5'-CCAGGAGATTCCAC-3' (SEQ ID NO.: 17) containing either phosphodiester internucleotide linkages or two phosphoromonothioate or two phosphorodithioate internucleotide linkages were synthesized and analyzed using the same gradient on a Mono Q column. The retention time of the phosphodiester oligonucleotide was 43.8 min, compared to 47.1 min for the phosphoromonothioate and 56.8 min for the phosphorodithioate oligonucleotides. It is clearly evident that the phosphodiester, phosphoromonothioate and phosphorodithioate were well separated.

The retention times of the oligonucleotide phosphorodithioate using a Mono Q column and a linear gradient of buffers A and B were listed.

The Mono Q purified oligonucleotide phosphorodithioates below were shown to be absent of any monothioate contamination by $^{31}$P NMR.

affinity of the dithioate aptamers is attributable at least in part to electrostatic effects.

EXAMPLE 6

Bio-activity of NF-κB Specific Thioaptamers

A. LPS Model

Figure 11A:
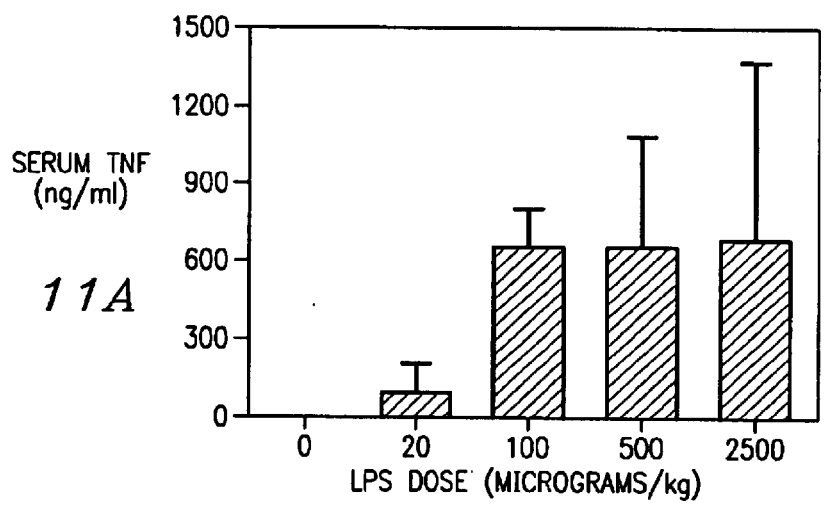
FIG. 11a shows the dose response curve of LPS administration on serum TNF in a guinea pig model.

Outbred Hartley guinea pigs (400 gm, male) were inoculated intraperitoneally with doses of lipopolysaccharide (*E. Coli* 011:B4). Blood samples collected 2 hours later were assayed for tumor necrosis factor (TNF) by standard bioassay. FIG. 11a shows the dose relationship between LPS dose and serum TNF. Each bar represents the mean with standard deviation of an assay with three animals per group.

B. Effect of Thioaptamer Administration on TNF Response

Figure 11B:
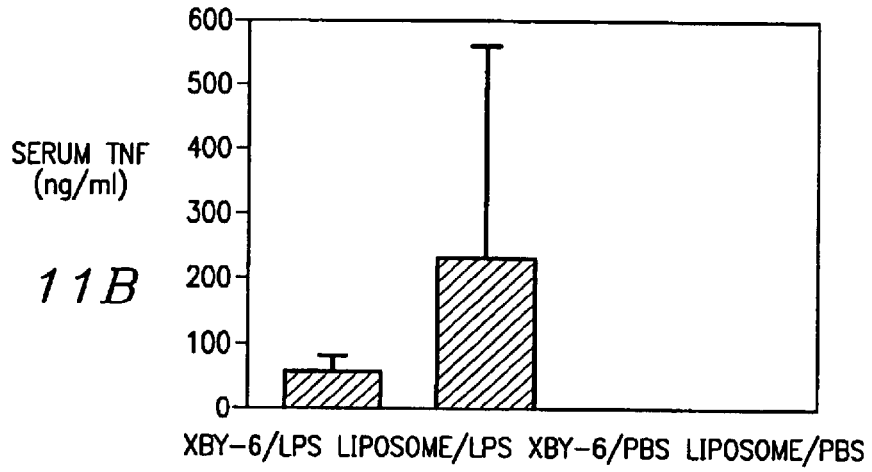
FIG. 11b shows the in vivo effect of a NF-kB specific thioaptamer on reducing serum TNF production in response to LPS challenge.

Guinea pigs were pre-treated with intraperitoneal inoculation of XBY-6 (SEQ ID NO.: 39) (50 μg in Tfx-50 liposomes, Promega), or empty liposomes, 1 hour before challenge with 100 μg/kg LPS or diluent alone (PBS). Serum TNF levels at 2 hours post LPS challenge are shown on FIG. 11b. Each bar represents average of 2 animals per group. The data graphed in FIGS. 11a and 11b demonstrate the in vivo physiologic deactivation of serum TNF production in mice

```
FPLC

Buffer A: 25 mM Tris-HCl, 1 mM EDTA, pH = 8
Buffer B: 25 mM Tris-HCl, 1 mM EDTA, 1 M NaCl, pH = 8

Condition:   Time    B%
             0.0     0.0
             80.0    100
             84.20   100
             85.40   0.0
             89.0    0.0
             90.0    0.0
```

| ID | Sequence | Rt | SEQ ID NO. |
|---|---|---|---|
| A025: | 5'-CCAG GA GA TTCC AC-3' | Rt = 43.8 06 | (SEQ ID NO.: 17) |
| A025: | 5'-CCAG GA GA T$_s$T$_s$CC AC-3' | Rt = 46.156, 47.125, 48.313 | (SEQ ID NO.: 42) |
| A036: | 5'-GTGGAAT$_{s2}$CT$_{s2}$CCTGG -3' | Rt = 56.905 | (SEQ ID NO.: 32) |
| A037: | 5'-GT$_{s2}$GGAATCTCCT$_{s2}$GG -3' | Rt = 57.870 | (SEQ ID NO.: 31) |
| B37: | 5'-CCAG GA GA T$_{s2}$T$_{s2}$CC AC-3' | Rt = 56.833 | (SEQ ID NO.: 30) |
| A070: | 5'-CCA$_{s2}$G GA GA TTCC A$_{s2}$C-3' | Rt = 57.265 | (SEQ ID NO.: 43) |
| A071: | 5'-CCAG GA$_{s2}$ GA$_{s2}$ TTCC AC-3' | Rt = 58.983 | (SEQ ID NO.: 44) |
| A072: | 5'-CCA$_{s2}$G GA$_{s2}$ GA$_{s2}$ TTCC AC-3' | Rt = 65.738 | (SEQ ID NO.: 45) |
| A073: | 5'-CCAG GA$_{s2}$ GA$_{s2}$ TTCC A$_{s2}$C-3' | Rt = 67.791 | (SEQ ID NO.: 46) |
| B38: | 5'-GT$_{s2}$GGAAT$_{s2}$CT$_{s2}$CCT$_{s2}$GG -3' | Rt = 73.326 | (SEQ ID NO.: 33) |
| A069: | 5'-CCA$_{s2}$G GA$_{s2}$ GA$_{s2}$ TTCC A$_{s2}$C-3' | Rt = 75.568 | (SEQ ID NO.: 47) |
| B51: | 5'-CCA$_{s2}$G $_{s2}$GA GA T$_{s2}$T$_{s2}$CC AC-3' | Rt = 77.805 | (SEQ ID NO.: 48) |

The variation in the retention times of the dithioates supports the observation by the present inventors that a major contributor to the inherent "stickiness" of the dithioates is the result of the poor cation binding by the dithioate relative to the normal phosphoryl group in the aptamers. Thus, with increasing numbers of dithioates shown in the above table, higher concentrations of NaCl are required to desorb the bound aptamer from the anion-exchange column. Aptamers with two, three or four dithioates, e.g., show an average retention time of 56 min (ca. 0.7 M NaCl), 66 min (ca. 0.83 M NaCl), and 75 min (0.94 M NaCl), respectively. This retention data provides confirmation that the enhanced treated with the XBY-6 aptamer developed using the method of the present invention.

While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

What is claimed is:

1. An aptamer that binds to one or more NF-κB/Rel proteins selected from the group consisting of:
   a) single stranded oligonucleotides identified by SEQ ID NO.: 39, wherein between one and six of the nucleotides are dithiophosphates;
   b) double stranded oligonucleotides in accordance with the sequence identified SEQ ID NO.: 39, wherein between one and ten of the nucleotides are dithiophosphates;
   c) single stranded oligonucleotides identified by SEQ ID NO.: 39, wherein between one and six of the nucleotides are dithiophosphates; and
   d) double stranded oligonucleotides in accordance with the sequence identified by SEQ ID NO.: 39, wherein between one and ten of the nucleotides are dithiophosphates.

2. The aptamer of claim 1, having the thioate and sequence substitutions of the oligonucleotides identified by SEQ ID NO.: 30–39.

3. The aptamer of claim 1, having the sequence of the formula:

5'-CCAGGAGAT$_{S2}$T$_{S2}$CCAC-3'

3'-GG$_{S2}$TCC$_{S2}$TC$_{S2}$TAAGG$_{S2}$TG-5'  (SEQ ID NO.: 39).

4. The aptamer of claim 1, further comprising one or more pharmaceutically acceptable salts.

5. The aptamer of claim 1, further comprising a diluent.

6. The aptamer of claim 1, wherein the aptamer is achiral.

7. The aptamer of claim 1, wherein the one or more NF-κB/Rel proteins comprises and NF-κB homodimer.

8. The aptamer of claim 1, wherein the one or more NF-κB/Rel proteins comprises an NF-κB heterodimer.

9. The aptamer of claim 1, further comprising an NF-κB/Rel protein bound to the aptamer.

10. The aptamer of claim 1, wherein the aptamer comprises one or more achiral thiomonophosphates.

11. The aptamer of claim 1, wherein the aptamer comprises one or more dithiophosphates.

12. A partially thio-modified aptamer that binds to an NF-κB/Rel protein.

13. A aptamer of claim 12, wherein the NF-κB/Rel protein comprises a human NF-κB.

14. The aptamer of claim 12, wherein the NF-κB/Rel protein comprises an NF-κB homodimer.

15. The aptamer of claim 12, wherein the NF-κB/Rel protein comprises and NF-κB heterodimer.

16. The aptamer of claim 12, wherein the aptamer comprises one or more thio-modifications as set forth in SEQ ID NOS.: 32, 33 and 38.

17. The aptamer of claim 12, wherein the aptamer further comprises a fluorescent label.

18. The aptamer of claim 12, further comprising one or more pharmaceutically acceptable salts.

19. The aptamer of claim 12, further comprising a diluent.

20. The aptamer of claim 12, wherein the aptamer is achiral.

21. A partially thio-modified aptamer the binds to human NF-κB protein complex.

* * * * *